United States Patent
Dietrich et al.

(10) Patent No.: US 6,248,328 B1
(45) Date of Patent: *Jun. 19, 2001

(54) HIV-1 VIRUS ISOLATES OF A SUBTYPE AND ITS DIFFERENTIAL DIAGNOSTICS, A VACCINE AGAINST HIV-1 VIRUS INFECTIONS OF THIS SUBTYPE AND METHOD OF PRODUCING SAME, USE OF THE HIV-1 VIRUS ISOLATES

(75) Inventors: Ursula Dietrich, Eschborn; Hagen Von Briesen, Hunstetten; Manuel Grez, Dossenheim; Helga Rubsamen-Waigmann, Bad Soden, all of (DE)

(73) Assignee: Chemotherapeutisches Forschungsinstitut, Frankfurt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/257,490

(22) Filed: Feb. 25, 1999

Related U.S. Application Data

(63) Continuation of application No. 08/392,806, filed on Apr. 20, 1995, now Pat. No. 5,965,135, which is a continuation of application No. PCT/EP93/02275, filed on Aug. 25, 1993.

(30) Foreign Application Priority Data

Aug. 29, 1992 (DE) .................................................. 42 28 787

(51) Int. Cl.$^7$ .......................... A61K 39/00; A61K 39/38; A61K 39/21; C07K 1/00; C07K 16/00
(52) U.S. Cl. .................................... 424/188.1; 424/184.1; 424/208.1; 530/395; 530/350; 530/324; 530/325; 530/326; 530/327; 530/328; 530/329; 435/5; 435/7.1; 435/7.2
(58) Field of Search .............................. 424/188.1, 184.1, 424/208.1; 530/395, 350, 324–329; 435/5, 7.1, 7.2

(56) References Cited

U.S. PATENT DOCUMENTS

| | | |
|---|---|---|
| 5,030,449 | 7/1991 | Berzofsky et al. . |
| 5,128,319 | 7/1992 | Arlinghaus . |

FOREIGN PATENT DOCUMENTS

| | | |
|---|---|---|
| 0 498 905 | 8/1982 | (EP) . |
| 0 327 180 | 8/1989 | (EP) . |
| 2 657 017 | 7/1991 | (FR) . |
| 2 677 364 | 12/1992 | (FR) . |
| WO 88/10267 | 12/1988 | (WO) . |
| WO 92/05800 | 4/1992 | (WO) . |

OTHER PUBLICATIONS

Dietrich, et al. : Detection of highly divergent HIV strains in India: Int. Conf. AIDS: 8(2): pA12 (abstract No. PoA 2055), Jul. 1992.*
Cohen, J. : Jitters Jeopardize Aids Vaccine Trials: Science: vol.262: p. 980–981 : 1993.*
Dietrich, et al: Detection of Highly Divergent HIV Strains in India: Int. Conf. AIDS (Netherlands): 8 (a) p1. .2 : Abstract No. PoA 2055: 1992.*
International Search Report, PCT/EP 93/02275, Feb. 11, 1994.
International Preliminary Examination Report, PCT/EP 93/02275, Dec. 9, 1994.

* cited by examiner

*Primary Examiner*—Brett L. Nelson
(74) *Attorney, Agent, or Firm*—Jacobson Holman, PLLC

(57) ABSTRACT

Three new HIV-1 isolates HIV-1 D747(ECACC V92082718), HIV-1 D757(ECACC V92082719) and HIV-1 D760(ECACC V92082720) are disclosed, which represent a further independent subtype of the HIV-1 family and have been recovered from Indian patients which at the time when the virus was isolated showed no typical AIDS symptoms. Also disclosed are vaccines against HIV-1 infections by this subtype and a process for producing the same, as well as the use of the HIV-1 infection, as well as for differential diagnosis.

7 Claims, No Drawings

HIV-1 VIRUS ISOLATES OF A SUBTYPE AND ITS DIFFERENTIAL DIAGNOSTICS, A VACCINE AGAINST HIV-1 VIRUS INFECTIONS OF THIS SUBTYPE AND METHOD OF PRODUCING SAME, USE OF THE HIV-1 VIRUS ISOLATES

This is a continuation of application Ser. No. 08/392,806 filed Apr. 20, 1995 now U.S. Pat. No. 5,965,135, which in turn is a § 371 of PCT/EP93/02275, filed Aug. 25, 1993, the disclosures of which are incorporated by reference, herein.

The invention relates to new HIV-1 virus isolates of a subtype, vaccines against HIV-1 virus infections of this subtype, methods of producing same, and the use of the virus isolates for the production of vaccines and for differential diagnostics.

Hitherto, efforts to develop agents for the prophylaxis and stherapy of HIV infections have focused on the inhibition of the reverse transcriptase or some other enzyme of the HIV-1 virus such as, for example, protease. Thereby a specific inhibition of viral replication in contrast to cellular replication is intended to be accomplished. Nevertheless, the antiviral agents of prior art suffer from the drawback that they are accompanied by a relatively high toxicity towards the cells, i.e. they do not only affect the virus.

Those groups of substances which have been identified as being active against HIV viruses include, inter alia, various nucleoside analogues (azidothymidine, di-deoxyinosine and di-deoxycytidine). However, a massive formation of resistence of the virus has been detected after some relatively short periods of therapy with these substances {Zimmermann et al., Abstract No. 3656, IV International Conference on AIDS, Stockholm, 1988, R übsamen-Waigmann et al., Infection 19, Suppl. 2, 77–82, 1991}. Furthermore, all of the substances mentioned produce considerable side-effects, at least when applied in higher doses.

Another inhibitor of reverse transcriptase is the substance Suramin. However, this substance, due to its toxicity towards the mammal organism, is also not suitable for prophylaxis or therapy of HIV-virus infections {H. Mitsuya et al. "Suramin Protection of T-Cells in vitro against Infectivity and Cyto-pathic Effect of HTLV-III, Science 226 (1984), pages 172–174}.

Further development has led to reverse transcriptase inhibitors which are less toxic towards the mammal organism. These include substances such as dextran sulfate and pentosan polysulfate, which have proven to display a HIV-1-inhibiting effect in vivo, as has been described in DE 36 01 136 and in EP 0 293 826.

In addition to a chemotherapeutic treatment of HIV infections there is basically the possibility of a gene therapy or immunotherapy. Gene therapy comprises the incorporation of parts of viral nucleic acids in human cells, especially in the target cells of the HIV virus, for example the CD4-positive cells of the immune system. Then, the viral messenger RNA (m-RNA) can be neutralized by the formation of an "antisense" RNA, i.e. an RNA complementary to m-RNA, and hence the virus proliferation can be terminated. In some other form, oligonucleotides or structures chemical related thereto that are complementary to m-RNA can be employed. In immunotherapy, antigens are administered after the infection which are expected to support the immune response to HIV.

Meanwhile, the World Health Organization (WHO) estimates a number of at least 13 million of HIV-infected people worldwide; no country has been left free from infections with HIV-1 or HIV-2 or both viruses at the same time. It is urgently necessary to develop a vaccine for protection from HIV infections in order to prevent the epidemic from farther spreading. Here, and also in immunotherapy, the main problem is the high variability of the HIV viruses: a prophylactic inoculation should and must include all of the possible virus variants. Epidemiologic investigations in combination with the genetic characterization of the viruses produced the result that several subtypes do already exist in both virus families {Myers et al., Human Retroviruses and AIDS, Los Alamos, 1991; Dietrich et al., Nature 342, 948–950, 1989}, which subtypes are significantly distinguished from one another with respect to their hereditary information to a degree such that one single vaccine will not be capable to be active against all variants. Moreover, these subtypes are also subject to different geographic distributions.

The present invention provides three new HIV 1 virus isolates HIV-$1_{D757}$, HIV-$1_{D747}$, HIV-$1_{D760}$, which, surprisingly, form a further independent subtype of the HIV-1 family and have been recovered from three Indian patients who, at the time of virus isolation, did not show any typical AIDS symptoms. Furthermore, the invention also includes virus isolates of the HIV-1 type which are up to 30%, and preferably up to 5%, divergent from HIV-$1_{D757}$, HIV-$1_{D747}$, and HIV-$1_{D760}$.

The virus isolates, in accordance with the regulations according to the Budapest Treaty, have been deposited with the European Collection of Animal Cell Cultures (ECACC), Porton Down, Salisbury, Wiltshire, United Kingdom, on Aug. 27, 1992, under the following Accession Numbers:

HIV-$1_{D747}$—ECACC V92082718
HIV-$1_{D757}$—ECACC V92082719
HIV-$1_{D760}$—ECACC V92082720

The virus isolates proliferate on fresh mononuclear cells of peripheral blood, i.e. lymphocytes and macrophages.

The invention further provides a vaccine having an activity spectrum against this specific HIV-1 subtype.

The vaccine contains, as the active ingredient, the peptides

1. MPNGTKSNS SEQ ID NO:7, MPNGTKGNS SEQ ID NO:8, MPNGTKSNL SEQ ID NO:9,
2. RNEKDLLALDSWKN SEQ ID NO:10, combinations comprising said peptides or longer or shorter subpeptides thereof being up to 7 amino acids in length.

Said peptides are derived from the env region of the strains according to the invention (cf. FIG. 1). The nucleotide sequences of these viruses in the env gene over a range of 1.8 kb are only to 79.4–81.6% homologous with viruses of the North American/European subtype and to 78.9–81.2% homologous with prototype viruses of the Central African subtype. The homology on the amino acid level is 72.1–75.9% and 71.2–74.2%, respectively (cf. Table). Thus, these viruses genetically are to be classified between these two subtypes and form some further independent subtype which is also distinguished from the subtypes found in Rwanda/Uganda and in Northern Thailand by genetic equidistance.

Upon comparison of the amino acid sequences of the env proteins of HIV-$1_{D757}$, HIV-$1_{D747}$, HIV-$1_{D760}$ with the consensus sequences as derived for all of the HIV env sequences already published, there result for the env region two short ranges, in which the three Indian sequences are different from all of the other HIV-1 sequences in 7 of 9 and in 7 of 14 amino acids, respectively (FIG. 1). Peptides from these regions are preferably suitable for a vaccine having a specific spectrum of activity against the Indian subtype, and particularly so, if the vaccine consists of a combination of these peptides.

The peptides according to the invention are synthetically produced and, if advantageous, are chemically modified. These peptides or longer as well as shorter subpeptides, down to 7 amino acids in length, thereof are also a constituent of this invention, and so are their modified forms.

Furthermore, the invention also relates to a vaccine which contains, as the active ingredient, peptides from variable regions of other genes of HIV-$1_{D757}$, HIV-$1_{D747}$, HIV-$1_{D760}$, if the deviation from the corresponding sequence of HIV-1 viruses of other subtypes is more than 30%.

In the vaccine, there may further be used antigens from the viruses according to the invention or peptide combinations or combinations of peptides and antigens. More specifically, the use of such antigens or peptides is preferred which, within the loop of the coat glycoprotein (amino acids 423–450, relative to HIV-$1_{Lai}$), is responsible for binding to the CD4-receptor, contain a glycosylation site (NXT/S) immediately in front of cysteine 450 (HIV-$1_{Lai}$). This glycosylation site is typical for the Indian viruses HIV-$1_{D757}$, HIV-$1_{D747}$ and HIV-$1_{D760}$. The amino acid regions of the HIV-$1_{D757}$, HIV-$1_{D747}$ and HIV-$1_{D760}$ that correspond to the amino acids 423–450 of HIV-$1_{Lai}$ are amino acids 294–321 of SEQ ID NO:2, amino acids 296–323 of SEQ ID NO:4, or amino acids 304–331 of SEQ ID NO:6 respectively. This glycosylation site has not been encountered among 29 HIV-1 env-genes that have been sequenced worldwide.

One preferred embodiment is a vaccine which is employed for prophylaxis prior to infections. Another preferred embodiment consists of that the vaccine is used as an immunotherapeutic to be employed after the infection and also covers the spectrum of variants of this subtype. The vaccine is administered either for injection with adjuvant or as an oral, genital or rectal form of application, e.g. via nanoparticles.

Furtheron, the subject matter of the invention comprises a process for producing a vaccine against HIV-1 virus infections from the viruses HIV-$1_{D757}$, HIV-$1_{D747}$ and HIV-$1_{D760}$ as well as the use of these viruses for the production of a vaccine.

In still one further embodiment, the viruses HIV-$1_{D757}$1 HIV-$1_{D747}$ and HIV-$1_{D760}$ are transferred into a suitable host animal and allowed to proliferate therein. Then, the antibodies formed, after appropriate work-up as also known in the art for other vaccines, are used as a passive vaccine against HIV virus infections. As the host animals, more particularly, there may be used, suitable types of monkeys, but also animals that can be immunized without developing HIV symptoms (e.g. rabbits) {Filice et al., Nature 335 (1988), 366–368}.

Human monoclonal antibodies against HIV-$1_{D757}$, HIV-$1_{D747}$ and HIV-$1_{D760}$ are also suitable for producing a vaccine for a protection against HIV-1 virus infections of this subtype.

In a further embodiment, in a suitable vector, DNA from which a RNA complementary to the viral m-RNA can be fully or partially transcribed, is transfected into human cells of the immune system and, hence, is conveyed into man. Thus, the viral m-RNA is competitively excluded from the further augmentation cycle. Likewise, synthetic oligonucleotides can be used for neutralizing the viral m-RNA.

In addition to the applications for therapy and vaccine production, HIV-$1_{D757}$, HIV-$1_{D747}$ and HIV-$1_{D760}$ can also be used for differential diagnostics in order to distinguish infections with this subtype from other subtypes. For differential diagnostics, selected regions of the DNA of HIV-$1_{D757}$, HIV-$1_{D747}$ and HIV-$1_{D760}$ are utilized which either do not occur at all in the prototype HIV-$1_{Lai}$ or are significantly different therefrom (by more than 30%). From these regions, peptides or nucleic acids for diagnostics are prepared according to conventional methods (labelling with radioactive isotopes, immunofluorescence test, ELISA etc.).

Therefore, it is also a constituent of this invention to use HIV-$1_{D757}$, HIV-$1_{D747}$ and HIV-$1_{D760}$, or antigens, peptides or nucleic acids thereof, for the differential diagnostics for differentiating between infections with the subtype, characterized by HIV-$1_{D757}$, HIV-$1_{D747}$ or HIV-$1_{D760}$, and infections with other HIV-1 subtypes as defined by the prototypes HIV-$1_{Lai}$ (U.S.A./Europe) HIV-$1_{Mal}$ (Central Africa), HIV-$1_{u455}$ (Uganda/Rwanda) and Northern Thailand.

It is also possible to employ peptide residues or PCR tests based on HIV-$1_{D757}$, HIV-$1_{D747}$ or HIV-$1_{D760}$, by means of which distinction can be made between viruses of this subtypes from other HIV-viruses.

Hereinbelow, the Figures and the Table are described:

The Table shows the nucleotide and amino acid sequence homology between HIV-$1_{D757}$, HIV-$1_{D747}$ or HIV-$1_{D760}$ and other HIV-1 virus subtypes in percent. The sequences were compared by using Mikrogenie™ sequencing software by the company Beckman.

Table 2 shows the amino acid sequences in single character notation of the three Indian env clones in comparison to the corresponding sections of other subtypes. Highlighted are the two peptides 1 and 2, in which the Indian subtype is mainly different from the other sequences, and the additional glycolisation site (underlined) in immediate vicinity to the CD4 binding domain.

(–) denotes identical amino acids;

(.) denotes missing aminoacids.

Table 3 shows the relation of the sequences HIV-$1_{D757}$, HIV-$1_{D747}$ or HIV-$1_{D760}$ to the remaining viruses in the phylogenetic tree of the viruses. This tree was established with the use of PAUP {Smith, T. F. et al., Nature 333, 573–575 (1988)} and the Version 3.21 of the PHYLIP bootstrappin algorithm.

TABLE 1

Homology of Indian HIV-1 isolates and American/European or prototypical African HIV-1 sequences (1.8 kb PCR-fragment, corresponding to positions 6129–7976 of HIV-$1_{Lai}$)

| HIV-1 | Lai | SF2 | Eli | Mal | SIVepz |
|---|---|---|---|---|---|
| D757 | 79.7 (75.7) | 81.6 (75.9) | 81.2 (74.2) | 80.6 (73.7) | 66.1 (61.2) |
| D747 | 79.4 (73.5) | 80.9 (75.6) | 80.7 (72.8) | 78.9 (73.2) | 65.8 (63.2) |
| D760 | 80.7 (72.1) | 81.4 (73.6) | 80.9 (71.2) | 80.2 (71.7) | 66.1 (61.0) |

TABLE 1-continued

Homology of Indian HIV-1 isolates and American/European or prototypical African HIV-1 sequences (1.8 kb PCR-fragment, corresponding to positions 6129–7976 of HIV-1$_{Lai}$)

| HIV-1 | Lai | SF2 | Eli | Mal | SIVcpz |
|---|---|---|---|---|---|
| Lai |  | 90.0 (84.1) | 83.7 (76.2) | 82.8 (74.3) | 65.0 (60.1) |
| SF2 |  |  | 83.8 (75.6) | 82.8 (74.6) | 64.3 (62.0) |
| Eli |  |  |  | 85.2 (76.9) | 65.7 (61.9) |
| Mal |  |  |  |  | 66.4 (63.2) |

TABLE 2

```
HIV-1_Bru    ------------------S-K--DLGNATN-NSSN.TNSSSGEMMMEKG--------IS-
HIV-1_SF2    ----------------------DLGKATN-NSSN.WKEEI......KG--------I--
HIV-1_D757   SLWDQSLKPCVKLTPLCVTLNCTNA...NVTYDN..........GNYTEEIKNCSFNTTT
HIV-1_D747   --------------------H----TYS-S--NS..........T.-N-----------
HIV-1_D760   --------------------E-G-VNAT-I-NNGE...NNPTNIT--R------P--A--
HIV-1_Eli    ----------------------SD-....ELRNNGTMGNNVTTEEK....GM------V--
HIV-1_Mal    ----------------------VNGTA-NGT-AGSNRTNAELKMEIG-V-------I-P
SIVcpz       --------------------Q-SK-NFSQA.......KNLTNQTSSPPL-M-------V--

HIV-1_Bru    SI-GKV--EY-F-----II-I-NDTT-......-T-TS----V----------E-------
HIV-1_SF2    SI--KI--EN---RN-----I-NASTTTNYTN----H--R-V----------E-------
HIV-1_D757   ELRDQKQKVAALFYKLDVVPLDGNDNSS....YRLINCNTSAITQACPKVSFDPIPIHYC
HIV-1_D747   ----K----Q-----------NTT----....----------------------------
HIV-1_D760   -I--RQ---Y----R--I----N-N--T....--------------------T--------
HIV-1_Eli    V-K-K--Q-Y----R--I---I-NDSSTNS.TN--------------------E-------
HIV-1_Mal    VGS-KR-E.Y-T--N--L-QI-D...-DN.SS----------V--------T---------
SIVcpz       ----K-KQ-YS---VE---N-GNEN-T......--I-----T---------T--E-------

HIV-1_Bru    ----F----------------T----VQ-----R--------------E-VV---A-FT
HIV-1_SF2    T---F-------------K---T----VQ-----R-I------------E-VV---D-FT
HIV-1_D757   APAGYAILKCNNKTFNGTGPCHNVSTRTCTHGIKPVVSTQLLLNGSLAEGEIIIRSENLA
HIV-1_D747   -G-------------------I--VQ----------------------------T
HIV-1_D760   -------------------------VQ-----S-----------------------T
HIV-1_Eli    ----F-----RD-K-------T----VQ-----R--------------E-V-----T
HIV-1_Mal    ----F------D-K----EI-K----VQ--------------------E--M------T
SIVcpz       ----F------D-D-S-K-K-T----VH---------T----I--------N-TV-V--KS HIV-1_Bru    D-A-----Q-----E-N--------------QR---RA-VTI-K-.-NM--------RA-
HIV-1_SF2    --A-----Q--E--A-N------------Y-..---RA-HT--R------K------RAQ
HIV-1_D757   NNVKTIIVHLNQSVRIVCTRPNNNTRKSIRI..GPGQTFYATGDIIGDIRQAHCNISEGK
HIV-1_D747   ---------------E--Y---------GV--..---Q--------------------KH-
HIV-1_D760   D-------------EV----------------..---Q---------------------D-
HIV-1_Eli    --A-N--A---E--K-T-A--YQ---QRTP-...L--SL-T-R.SRSI-G-------RAQ
HIV-1_Mal    D-T-N---Q--ET-T-N----G----RG-HF.-----AL-T--.-V-----R-Y-T-N-TE
SIVcpz       K-TDVW--Q-VEA-SLN-H--G----GEVQ-..---M---NIENVV--T-S-Y-K-NGTT
```

TABLE 2-continued

| | |
|---|---|
| HIV-1_Bru | --A--KQIAS--R-Q-G-N--.-I-KQ----DP-V------G-------STQ-----WF |
| HIV-1_SF2 | --N--EQIV---R-Q-G-N--.-V-NQ----DP--VM--------------TQLF..... |
| HIV-1_D757 | WNETLQRVGKKLAEYFPN.KT.IKFASSSGGGLEITTHSFNCRGEFFYCNTSNLFNSTY. |
| HIV-1_D747 | ---------------H---.---.-R-------D--------------------D---G--. |
| HIV-1_D760 | ---------------H---.---.----A----D-----Y---------------G---G--. |
| HIV-1_Eli | -SK---Q-AR--GTLL.-KTI.---KP----DP---------G---------G-----WN |
| HIV-1_Mal | -DK---Q-AV--GSLL.-KTK.-I-N-----DP-------------------K-----WQ |
| SIVcpz | --R-VEE-K-A--TSSNRTAAN-TLNRA---DP-V-H-M---G---------QI-..... |
| HIV-1_Bru | NSTWSTEGSNNTEGSD---LP-----F--------K-------S-Q-R-S---------T- |
| HIV-1_SF2 | NNTWRLNHTEGTKG-D--ILP--------------K-------G-Q-S-S---------T- |
| HIV-1_D757 | .....MPNGTKGNSNSTITIQCRIKQIINMWQEVGRAMYAPPIEGNITCESNITGLLLVR |
| HIV-1_D747 | .....-------S--S-----P---------------------A-----K-----I---- |
| HIV-1_D760 | .....-------S-L-------P-------V-L------------FAR----K---------- |
| HIV-1_Eli | ISAWNNITESNNST-TN--L--------K-.VAGRK-I------R--L-S--------T- |
| HIV-1_Mal | NNG.ARLSNSTESTG-.--LP-----------KT-K-------A-V-N-L------I-T- |
| SIVcpz | .........-DNIT-GI-ILP---R--VSS-MR---GI-----R-----N---------TS |
| HIV-1_Bru | ---NN.--G.S-I----------D------------K-E-------K------....Q--- |
| HIV-1_SF2 | ----NVT-D.T-V----------D------------IK-E---I---K------....Q--- |
| HIV-1_D757 | DGGTESNNT..ETFRPGGG-MRNNWRSELYKYKVVEIKPLGVAPTTAKRRVV....EREK |
| HIV-1_D747 | ---IEL-D-KT--------E--D-------------------------...---- |
| HIV-1_D760 | ---EDT-D..T-I-S--------D-------------------------...---- |
| HIV-1_Eli | ---..I--STN-----------D------------Q-E-------R------...---- |
| HIV-1_Mal | ---NS-D-SDN--L---------D--I---------R-E-------K------...---- |
| SIVcpz | -TPVTN-SGNL.----T--N-KDI-----------R-E--S----K-R-HT-ARQKD-Q- |
| HIV-1_Bru | -----.---L--------------R-------------N--------------- |
| HIV-1_SF2 | -----V--M---------------V-L---------------N--------------- |
| HIV-1_D757 | RAVGI.GAVFLGFLGAAGSTMGAASMTLTVQARQLLSGIVQQQSNLLRAIEAQQHLLQLT |
| HIV-1_D747 | -----.---------------------V-------------------------- |
| HIV-1_D760 | ----L.---------------------I-------------------------- |
| HIV-1_Eli | --I-L.--M--------------R-V---------M-------N--------------- |
| HIV-1_Mal | --I-L.--M--------------L-----------N--------------- |
| SIVcpz | --AFGL--L---------------AV-----------------N---K----------S |
| HIV-1_Bru | --------A-I--V--------------C--------A----A---.-K-LEQ------- |
| HIV-1_SF2 | --------A----V----R---------C--------A----A---.-K-LED------- |
| HIV-1_D757 | VWGIKQLQTRVLAIERYLKDQQLLGIWGRSGKLICTTNVPWNSSWS.NRSQTDIWDNMTW |
| HIV-1_D747 | I--------A-----------E--------C--------T---------.------------- |
| HIV-1_D760 | ------------------------M--C--------A--------.------------- |
| HIV-1_Eli | --------A-I--V--------------C---H--------------.---LNE--Q---- |
| HIV-1_Mal | --------A----V----Q--R---M--C--H----F---------.---LD---N---- |
| SIVcpz | I--V----A-L--V----Q---I--L--C----AV-Y-T-------PGSN-TD---G-L-- |

TABLE 2-continued

| | | |
|---|---|---|
| HIV-1_Bru | -E---..........................................--N---SL-HS-I-E | |
| HIV-1_SF2 | ---E-..........................................---D-N---T---E | |
| HIV-1_D757 | MQWDR.........................................EISNYTDTIYRLLED | |
| HIV-1_D747 | ------..........................................------E-------- | |
| HIV-1_D760 | ------..........................................------N-------- | |
| HIV-1_Eli | -E-E-..........................................---D---GL--S-I-E | |
| HIV-1_Mal | ---EK..........................................------GI--N-I-E | |
| SIVcpz | Q---KLVSNYTGKIFGLLEEAQSQQEKNERDLLELDQWASLWNWFD-T---GK-FG---E | |
| HIV-1_Bru | ------K--QE--E--K-AS-----N-------------------V--R-V---------- | |
| HIV-1_SF2 | ------K--QE--E--K-AS-------------------------V--R-V---------- | |
| HIV-1_D757 | SQNQQERNEKDLLALDSWKNLWNWFSITNWLWYIKIFIMIVGGLIGLKIIFAVLSIVNRV | |
| HIV-1_D747 | ----------------------------------------I--------R------C----- | |
| HIV-1_D760 | ----------------------------------------------------R------------- | |
| HIV-1_Eli | --T---K---E-E--K-AS--------Q-----------I------R-V-----L---- | |
| HIV-1_Mal | --I---K---E-E--K-AS-------SK-----R---IV-------R-------L---- | |
| SIVcpz | A-S---K--R---E--Q-AS-----D--K--------L-A---I---R--MT-F-V-R-- |
| HIV-1_Bru | ----------- SEQ ID NO: 11 |
| HIV-1_SF2 | ----------- SEQ ID NO: 12 |
| HIV-1_D757 | RQGYSPLSFQT SEQ ID NO: 2 |
| HIV-1_D747 | KA--------- SEQ ID NO: 4 |
| HIV-1_D760 | ----------- SEQ ID NO: 6 |
| HIV-1_Eli | ----------- SEQ ID NO: 13 |
| HIV-1_Mal | --------L-- SEQ ID NO: 14 |
| SIVcpz | --------L-- SEQ ID NO: 15 |

TABLE 3

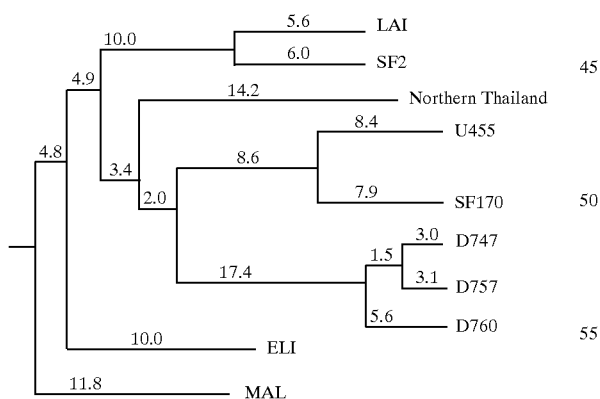

What is claimed is:

1. A peptide having antigenic properties, wherein the peptide is a sub-peptide of amino acids 294–321 of SEQ ID NO:2, amino acids 296–323 of SEQ ID NO:4, or amino acids 304–331 of SEQ ID NO:6, wherein the sub-peptide includes the sequence NXT or NXS, and wherein the sub-peptide has a length of at least 7 amino acids.

2. The peptide according to claim 1, produced from an HIV-1 isolate selected from the group consisting of the virus HIV-1$_{D757}$, the virus HIV-1$_{D747}$, the virus HIV-1$_{D760}$, or a combination, thereof.

3. The peptide according to claim 2, produced from the virus HIV-1$_{D757}$.

4. The peptide according to claim 2, produced from the virus HIV-1$_{D747}$.

5. The peptide according to claim 2, produced from the virus HIV-1$_{D760}$.

6. The peptide according to claim 1, produced by chemical synthesis.

7. A process for producing antibodies comprising injecting an animal with the peptide according to claim 1, and recovering the antibodies produced by the animal in response to the peptide.

* * * * *

SEQUENCE LISTING

<160> NUMBER OF SEQ ID NOS: 15

<210> SEQ ID NO: 1
<211> LENGTH: 1932
<212> TYPE: DNA
<213> ORGANISM: Human immunodeficiency virus
<220> FEATURE:
<223> OTHER INFORMATION: HIV-1(D757)
<220> FEATURE:
<221> NAME/KEY: CDS
<222> LOCATION: (2)..(1789)

<400> SEQUENCE: 1

```
c agt tta tgg gat caa agc cta aag cca tgt gta aag ttg acc cca ctc      49
  Ser Leu Trp Asp Gln Ser Leu Lys Pro Cys Val Lys Leu Thr Pro Leu
   1               5                   10                  15 tgt gtc act tta aat tgt aca aat gca aat gtt acc tat gat aat ggt       97
Cys Val Thr Leu Asn Cys Thr Asn Ala Asn Val Thr Tyr Asp Asn Gly
             20                  25                  30 aac tac act gaa gaa ata aaa aat tgc tct ttc aat aca act aca gaa      145
Asn Tyr Thr Glu Glu Ile Lys Asn Cys Ser Phe Asn Thr Thr Thr Glu
         35                  40                  45 cta aga gat cag aaa cag aaa gtt gct gca ctt ttt tat aaa ctt gat      193
Leu Arg Asp Gln Lys Gln Lys Val Ala Ala Leu Phe Tyr Lys Leu Asp
     50                  55                  60 gta gta cca ctt gat ggt aat gat aac tct agt tat aga tta ata aat      241
Val Val Pro Leu Asp Gly Asn Asp Asn Ser Ser Tyr Arg Leu Ile Asn
 65                  70                  75                  80 tgt aat acc tca gcc ata aca caa gcc tgt cca aag gtc tct ttt gac      289
Cys Asn Thr Ser Ala Ile Thr Gln Ala Cys Pro Lys Val Ser Phe Asp
                 85                  90                  95 cca atc cct ata cat tat tgt gct cca gct ggt tat gcg att cta aag      337
Pro Ile Pro Ile His Tyr Cys Ala Pro Ala Gly Tyr Ala Ile Leu Lys
            100                 105                 110 tgt aat aat aag aca ttc aat ggg aca gga cca tgc cat aat gtc agc      385
Cys Asn Asn Lys Thr Phe Asn Gly Thr Gly Pro Cys His Asn Val Ser
        115                 120                 125 aca cgt aca tgt aca cat gga att aag cca gta gta tca act caa cta      433
Thr Arg Thr Cys Thr His Gly Ile Lys Pro Val Val Ser Thr Gln Leu
    130                 135                 140 ctg tta aat ggt agc cta gca gaa gga gag ata ata att aga tct gaa      481
Leu Leu Asn Gly Ser Leu Ala Glu Gly Glu Ile Ile Ile Arg Ser Glu
145                 150                 155                 160 aat ctg gca aac aat gtc aaa aca ata ata gta cat ctt aat caa tct      529
Asn Leu Ala Asn Asn Val Lys Thr Ile Ile Val His Leu Asn Gln Ser
                165                 170                 175 gta aga att gtg tgt aca aga ccc aac aat aat aca aga aaa agt ata      577
Val Arg Ile Val Cys Thr Arg Pro Asn Asn Asn Thr Arg Lys Ser Ile
            180                 185                 190 agg ata gga cca gga caa aca ttc tat gca aca gga gac ata ata gga      625
Arg Ile Gly Pro Gly Gln Thr Phe Tyr Ala Thr Gly Asp Ile Ile Gly
        195                 200                 205 gac ata aga caa gca cat tgt aac att agt gaa ggt aaa tgg aat gaa      673
Asp Ile Arg Gln Ala His Cys Asn Ile Ser Glu Gly Lys Trp Asn Glu
    210                 215                 220 act tta caa agg gta ggt aaa aaa tta gca gaa tac ttc cct aat aaa      721
Thr Leu Gln Arg Val Gly Lys Lys Leu Ala Glu Tyr Phe Pro Asn Lys
225                 230                 235                 240 aca ata aaa ttt gca tca tcc tca gga ggg ggc cta gaa att aca aca      769
Thr Ile Lys Phe Ala Ser Ser Ser Gly Gly Gly Leu Glu Ile Thr Thr
```

-continued

```
                    245                 250                 255
cat agc ttt aat tgt aga gga gaa ttt ttc tat tgc aat aca tca aac      817
His Ser Phe Asn Cys Arg Gly Glu Phe Phe Tyr Cys Asn Thr Ser Asn
            260                 265                 270 ctg ttt aat agt aca tac atg cct aat ggt aca aaa ggt aat tca aac      865
Leu Phe Asn Ser Thr Tyr Met Pro Asn Gly Thr Lys Gly Asn Ser Asn
            275                 280                 285 tca acc atc aca atc caa tgc aga ata aaa caa att ata aac atg tgg      913
Ser Thr Ile Thr Ile Gln Cys Arg Ile Lys Gln Ile Ile Asn Met Trp
            290                 295                 300 cag gag gta gga cga gca atg tat gcc cct ccc att gaa gga aac ata      961
Gln Glu Val Gly Arg Ala Met Tyr Ala Pro Pro Ile Glu Gly Asn Ile
305                 310                 315                 320 acg tgt gaa tcc aat atc aca gga cta cta ttg gta cgt gat gga gga     1009
Thr Cys Glu Ser Asn Ile Thr Gly Leu Leu Leu Val Arg Asp Gly Gly
                325                 330                 335 aca gag tca aat aat aca gag aca ttc aga cct gga gga gga gat atg     1057
Thr Glu Ser Asn Asn Thr Glu Thr Phe Arg Pro Gly Gly Gly Asp Met
                340                 345                 350 agg aac aat tgg aga agt gaa tta tat aaa tat aaa gtg gta gaa att     1105
Arg Asn Asn Trp Arg Ser Glu Leu Tyr Lys Tyr Lys Val Val Glu Ile
            355                 360                 365 aag cca ttg gga gta gcg ccc act act gca aaa agg aga gtg gtg gag     1153
Lys Pro Leu Gly Val Ala Pro Thr Thr Ala Lys Arg Arg Val Val Glu
370                 375                 380 aga gaa aaa aga gca gtg gga ata gga gct gtg ttc ctt ggg ttc ttg     1201
Arg Glu Lys Arg Ala Val Gly Ile Gly Ala Val Phe Leu Gly Phe Leu
385                 390                 395                 400 gga gca gca gga agc act atg ggc gcg gca tca atg acg ctg acg gta     1249
Gly Ala Ala Gly Ser Thr Met Gly Ala Ala Ser Met Thr Leu Thr Val
                405                 410                 415 cag gcc aga caa ttg ttg tct ggt ata gtg caa cag caa agc aat ttg     1297
Gln Ala Arg Gln Leu Leu Ser Gly Ile Val Gln Gln Gln Ser Asn Leu
                420                 425                 430 ctg agg gct ata gag gcg caa cag cat ctg ttg caa ctc acg gtc tgg     1345
Leu Arg Ala Ile Glu Ala Gln Gln His Leu Leu Gln Leu Thr Val Trp
            435                 440                 445 ggc att aag cag ctc cag aca aga gtc ctg gct ata gaa aga tac cta     1393
Gly Ile Lys Gln Leu Gln Thr Arg Val Leu Ala Ile Glu Arg Tyr Leu
        450                 455                 460 aag gat caa cag ctc cta ggg att tgg ggc cgc tct gga aaa ctc atc     1441
Lys Asp Gln Gln Leu Leu Gly Ile Trp Gly Arg Ser Gly Lys Leu Ile
465                 470                 475                 480 tgc acc act aat gta cct tgg aac tcc agc tgg agt aac aga tct caa     1489
Cys Thr Thr Asn Val Pro Trp Asn Ser Ser Trp Ser Asn Arg Ser Gln
                485                 490                 495 aca gat att tgg gat aac atg acc tgg atg cag tgg gat aga gaa att     1537
Thr Asp Ile Trp Asp Asn Met Thr Trp Met Gln Trp Asp Arg Glu Ile
                500                 505                 510 agt aat tac aca gac aca ata tac agg ttg ctt gaa gac tcg caa aac     1585
Ser Asn Tyr Thr Asp Thr Ile Tyr Arg Leu Leu Glu Asp Ser Gln Asn
            515                 520                 525 cag cag gaa aga aat gaa aaa gat tta tta gca ttg gac agt tgg aaa     1633
Gln Gln Glu Arg Asn Glu Lys Asp Leu Leu Ala Leu Asp Ser Trp Lys
            530                 535                 540 aat ctg tgg aat tgg ttt agc ata aca aat tgg ctg tgg tat ata aaa     1681
Asn Leu Trp Asn Trp Phe Ser Ile Thr Asn Trp Leu Trp Tyr Ile Lys
545                 550                 555                 560 ata ttc ata atg ata gta gga ggc ttg ata ggt ttg aaa ata att ttt     1729
```

```
Ile Phe Ile Met Ile Val Gly Gly Leu Ile Gly Leu Lys Ile Ile Phe
                565                 570                 575 gct gtg ctc tct ata gtg aat aga gtt agg cag gga tac tca cct tta          1777
Ala Val Leu Ser Ile Val Asn Arg Val Arg Gln Gly Tyr Ser Pro Leu
            580                 585                 590 tcg ttt cag acc cttaccccga acccaggggg acccgacagg ctcgaaagaa              1829
Ser Phe Gln Thr
        595 tcgaaggagg aggtggagag caagacaaag acagatccat tcgcttagtg aacggattct        1889 tagcacttgc ctgggacgac tgcggagcct gtgcctcttc agc                          1932

<210> SEQ ID NO: 2
<211> LENGTH: 596
<212> TYPE: PRT
<213> ORGANISM: Human immunodeficiency virus
<220> FEATURE:
<223> OTHER INFORMATION: HIV-1(D757)

<400> SEQUENCE: 2

Ser Leu Trp Asp Gln Ser Leu Lys Pro Cys Val Lys Leu Thr Pro Leu
  1               5                  10                  15

Cys Val Thr Leu Asn Cys Thr Asn Ala Asn Val Thr Tyr Asp Asn Gly
             20                  25                  30

Asn Tyr Thr Glu Glu Ile Lys Asn Cys Ser Phe Asn Thr Thr Thr Glu
         35                  40                  45

Leu Arg Asp Gln Lys Gln Lys Val Ala Ala Leu Phe Tyr Lys Leu Asp
     50                  55                  60

Val Val Pro Leu Asp Gly Asn Asp Asn Ser Ser Tyr Arg Leu Ile Asn
 65                  70                  75                  80

Cys Asn Thr Ser Ala Ile Thr Gln Ala Cys Pro Lys Val Ser Phe Asp
                 85                  90                  95

Pro Ile Pro Ile His Tyr Cys Ala Pro Ala Gly Tyr Ala Ile Leu Lys
            100                 105                 110

Cys Asn Asn Lys Thr Phe Asn Gly Thr Gly Pro Cys His Asn Val Ser
        115                 120                 125

Thr Arg Thr Cys Thr His Gly Ile Lys Pro Val Val Ser Thr Gln Leu
    130                 135                 140

Leu Leu Asn Gly Ser Leu Ala Glu Gly Glu Ile Ile Arg Ser Glu
145                 150                 155                 160

Asn Leu Ala Asn Asn Val Lys Thr Ile Ile Val His Leu Asn Gln Ser
                165                 170                 175

Val Arg Ile Val Cys Thr Arg Pro Asn Asn Asn Thr Arg Lys Ser Ile
            180                 185                 190

Arg Ile Gly Pro Gly Gln Thr Phe Tyr Ala Thr Gly Asp Ile Ile Gly
        195                 200                 205

Asp Ile Arg Gln Ala His Cys Asn Ile Ser Glu Gly Lys Trp Asn Glu
    210                 215                 220

Thr Leu Gln Arg Val Gly Lys Lys Leu Ala Glu Tyr Phe Pro Asn Lys
225                 230                 235                 240

Thr Ile Lys Phe Ala Ser Ser Gly Gly Gly Leu Glu Ile Thr Thr
                245                 250                 255

His Ser Phe Asn Cys Arg Gly Glu Phe Phe Tyr Cys Asn Thr Ser Asn
            260                 265                 270

Leu Phe Asn Ser Thr Tyr Met Pro Asn Gly Thr Lys Gly Asn Ser Asn
        275                 280                 285
```

```
Ser Thr Ile Thr Ile Gln Cys Arg Ile Lys Gln Ile Ile Asn Met Trp
    290                 295                 300
Gln Glu Val Gly Arg Ala Met Tyr Ala Pro Pro Ile Glu Gly Asn Ile
305                 310                 315                 320
Thr Cys Glu Ser Asn Ile Thr Gly Leu Leu Leu Val Arg Asp Gly Gly
                325                 330                 335
Thr Glu Ser Asn Asn Thr Glu Thr Phe Arg Pro Gly Gly Gly Asp Met
            340                 345                 350
Arg Asn Asn Trp Arg Ser Glu Leu Tyr Lys Tyr Lys Val Val Glu Ile
        355                 360                 365
Lys Pro Leu Gly Val Ala Pro Thr Thr Ala Lys Arg Arg Val Val Glu
    370                 375                 380
Arg Glu Lys Arg Ala Val Gly Ile Gly Ala Val Phe Leu Gly Phe Leu
385                 390                 395                 400
Gly Ala Ala Gly Ser Thr Met Gly Ala Ala Ser Met Thr Leu Thr Val
                405                 410                 415
Gln Ala Arg Gln Leu Leu Ser Gly Ile Val Gln Gln Gln Ser Asn Leu
            420                 425                 430
Leu Arg Ala Ile Glu Ala Gln Gln His Leu Leu Gln Leu Thr Val Trp
        435                 440                 445
Gly Ile Lys Gln Leu Gln Thr Arg Val Leu Ala Ile Glu Arg Tyr Leu
    450                 455                 460
Lys Asp Gln Gln Leu Leu Gly Ile Trp Gly Arg Ser Gly Lys Leu Ile
465                 470                 475                 480
Cys Thr Thr Asn Val Pro Trp Asn Ser Ser Trp Ser Asn Arg Ser Gln
                485                 490                 495
Thr Asp Ile Trp Asp Asn Met Thr Trp Met Gln Trp Asp Arg Glu Ile
            500                 505                 510
Ser Asn Tyr Thr Asp Thr Ile Tyr Arg Leu Leu Glu Asp Ser Gln Asn
        515                 520                 525
Gln Gln Glu Arg Asn Glu Lys Asp Leu Leu Ala Leu Asp Ser Trp Lys
    530                 535                 540
Asn Leu Trp Asn Trp Phe Ser Ile Thr Asn Trp Leu Trp Tyr Ile Lys
545                 550                 555                 560
Ile Phe Ile Met Ile Val Gly Gly Leu Ile Gly Leu Lys Ile Ile Phe
                565                 570                 575
Ala Val Leu Ser Ile Val Asn Arg Val Arg Gln Gly Tyr Ser Pro Leu
            580                 585                 590
Ser Phe Gln Thr
        595

<210> SEQ ID NO: 3
<211> LENGTH: 1944
<212> TYPE: DNA
<213> ORGANISM: Human immunodeficiency virus
<220> FEATURE:
<223> OTHER INFORMATION: HIV-1(D747)
<220> FEATURE:
<221> NAME/KEY: CDS
<222> LOCATION: (131)..(1930)

<400> SEQUENCE: 3
taatgtctgg gcaacacatg cctgtgtacc cacagacccc aacccacaag agatggtttt    60
gggaaatgta acagaaaatt ttaacatgtg gagaaatgac atggtgaatc agatgcatga   120
ggatgtaatc agt tta tgg gat caa agc cta aag cca tgt gta aag ttg      169
            Ser Leu Trp Asp Gln Ser Leu Lys Pro Cys Val Lys Leu
```

-continued

```
        1                   5                       10
acc cca ctc tgt gtc act tta cat tgt aca aat gct acc tat agt aat    217
Thr Pro Leu Cys Val Thr Leu His Cys Thr Asn Ala Thr Tyr Ser Asn
        15                  20                      25 agt acc tac aat agt acc tac aat gaa gaa ata aaa aat tgc tct ttc    265
Ser Thr Tyr Asn Ser Thr Tyr Asn Glu Glu Ile Lys Asn Cys Ser Phe
30                      35                      40                  45 aat aca act acg gaa cta aga gat aag aaa cag aaa gta caa gca ctt    313
Asn Thr Thr Thr Glu Leu Arg Asp Lys Lys Gln Lys Val Gln Ala Leu
            50                      55                      60 ttt tat aaa ctt gat gta gta cca ctt aat act act gat aac tct agt    361
Phe Tyr Lys Leu Asp Val Val Pro Leu Asn Thr Thr Asp Asn Ser Ser
                65                      70                      75 tat aga tta ata aat tgt aat acc tca gcc ata aca caa gcc tgt cca    409
Tyr Arg Leu Ile Asn Cys Asn Thr Ser Ala Ile Thr Gln Ala Cys Pro
            80                      85                      90 aag gtc tca ttt gac cca att cct ata cat tat tgt gct gga gct ggt    457
Lys Val Ser Phe Asp Pro Ile Pro Ile His Tyr Cys Ala Gly Ala Gly
        95                      100                     105 tat gcg att cta aag tgt aat aat aag aca ttc aat ggg aca gga cca    505
Tyr Ala Ile Leu Lys Cys Asn Asn Lys Thr Phe Asn Gly Thr Gly Pro
110                     115                     120                 125 tgc cat aat atc agc aca gta caa tgt aca cat gga att aag cca gta    553
Cys His Asn Ile Ser Thr Val Gln Cys Thr His Gly Ile Lys Pro Val
                130                     135                     140 gta tca act caa cta ctg tta aat ggt agc cta gca gaa gga gag ata    601
Val Ser Thr Gln Leu Leu Leu Asn Gly Ser Leu Ala Glu Gly Glu Ile
            145                     150                     155 ata att aga tct gaa aat ctg aca aac aat gtc aaa aca ata ata gta    649
Ile Ile Arg Ser Glu Asn Leu Thr Asn Asn Val Lys Thr Ile Ile Val
            160                     165                     170 cat ctt aat caa tct gta gaa att gtg tat aca aga ccc aac aat aat    697
His Leu Asn Gln Ser Val Glu Ile Val Tyr Thr Arg Pro Asn Asn Asn
        175                     180                     185 aca agg aaa ggt gta agg ata gga cca gga caa aca ttc tat gca aca    745
Thr Arg Lys Gly Val Arg Ile Gly Pro Gly Gln Thr Phe Tyr Ala Thr
190                     195                     200                 205 gga gac ata ata gga gac ata aga caa gca cat tgt aac att agt aaa    793
Gly Asp Ile Ile Gly Asp Ile Arg Gln Ala His Cys Asn Ile Ser Lys
                210                     215                     220 cat aaa tgg aat gaa act tta caa agg gta ggt aaa aaa tta gca gaa    841
His Lys Trp Asn Glu Thr Leu Gln Arg Val Gly Lys Lys Leu Ala Glu
            225                     230                     235 cac ttc cct aat aaa aca ata aga ttt gca tca tcc tca gga ggg gac    889
His Phe Pro Asn Lys Thr Ile Arg Phe Ala Ser Ser Ser Gly Gly Asp
        240                     245                     250 cta gaa att aca aca cat agc ttt aat tgt aga gga gaa ttt ttc tat    937
Leu Glu Ile Thr Thr His Ser Phe Asn Cys Arg Gly Glu Phe Phe Tyr
        255                     260                     265 tgc aat aca tca gac ctg ttt aat ggt aca tac atg cct aat ggt aca    985
Cys Asn Thr Ser Asp Leu Phe Asn Gly Thr Tyr Met Pro Asn Gly Thr
270                     275                     280                 285 aaa agt aat tca agc tca acc atc aca att cca tgc aga ata aaa caa   1033
Lys Ser Asn Ser Ser Ser Thr Ile Thr Ile Pro Cys Arg Ile Lys Gln
                290                     295                     300 att ata aac atg tgg cag gag gta gga cga gca atg tat gcc cct ccc   1081
Ile Ile Asn Met Trp Gln Glu Val Gly Arg Ala Met Tyr Ala Pro Pro
            305                     310                     315 att gca gga aac ata acg tgt aaa tcc aat att aca gga ata cta ttg   1129
```

```
Ile Ala Gly Asn Ile Thr Cys Lys Ser Asn Ile Thr Gly Ile Leu Leu
            320                 325                 330 gta cgt gat gga gga ata gag cta aat gat aca aag aca gag aca ttc    1177
Val Arg Asp Gly Gly Ile Glu Leu Asn Asp Thr Lys Thr Glu Thr Phe
        335                 340                 345 aga ccg gga gga gga gaa atg agg gac aat tgg aga agt gaa tta tat    1225
Arg Pro Gly Gly Gly Glu Met Arg Asp Asn Trp Arg Ser Glu Leu Tyr
350                 355                 360                 365 aaa tat aaa gtg gta gaa att aag cca ttg gga gta gcg ccc act act    1273
Lys Tyr Lys Val Val Glu Ile Lys Pro Leu Gly Val Ala Pro Thr Thr
                370                 375                 380 gca aaa agg aga gtg gtg gag aga gaa aaa aga gca gtg gga ata gga    1321
Ala Lys Arg Arg Val Val Glu Arg Glu Lys Arg Ala Val Gly Ile Gly
            385                 390                 395 gct gta ttc ctt ggg ttc ttg gga gca gca gga agc act atg ggc gcg    1369
Ala Val Phe Leu Gly Phe Leu Gly Ala Ala Gly Ser Thr Met Gly Ala
        400                 405                 410 gcg tca atg acc gtg acg gta cag gcc aga caa ttg ttg tct ggt ata    1417
Ala Ser Met Thr Val Thr Val Gln Ala Arg Gln Leu Leu Ser Gly Ile
415                 420                 425 gtg caa cag caa agc aat ttg ctg agg gct ata gag gcg caa cag cat    1465
Val Gln Gln Gln Ser Asn Leu Leu Arg Ala Ile Glu Ala Gln Gln His
430                 435                 440                 445 ctg ttg caa ctc acg atc tgg ggg att aag cag ctc cag gca aga gtc    1513
Leu Leu Gln Leu Thr Ile Trp Gly Ile Lys Gln Leu Gln Ala Arg Val
                450                 455                 460 ctg gct ata gaa aga tac cta aag gaa caa cag ctc cta ggg att tgg    1561
Leu Ala Ile Glu Arg Tyr Leu Lys Glu Gln Gln Leu Leu Gly Ile Trp
            465                 470                 475 ggc tgc tct gga aaa ctc atc tgc acc act act gta cct tgg aac tcc    1609
Gly Cys Ser Gly Lys Leu Ile Cys Thr Thr Thr Val Pro Trp Asn Ser
        480                 485                 490 agt tgg agt aac aga tct caa aca gat att tgg gat aac atg acc tgg    1657
Ser Trp Ser Asn Arg Ser Gln Thr Asp Ile Trp Asp Asn Met Thr Trp
495                 500                 505 atg cag tgg gat aga gaa att agt aat tac aca gaa aca ata tac agg    1705
Met Gln Trp Asp Arg Glu Ile Ser Asn Tyr Thr Glu Thr Ile Tyr Arg
510                 515                 520                 525 ttg ctt gaa gac tcg caa aac cag cag gaa aga aat gaa aaa gat tta    1753
Leu Leu Glu Asp Ser Gln Asn Gln Gln Glu Arg Asn Glu Lys Asp Leu
                530                 535                 540 tta gca ttg gac agt tgg aaa aat ctg tgg aat tgg ttt agc ata aca    1801
Leu Ala Leu Asp Ser Trp Lys Asn Leu Trp Asn Trp Phe Ser Ile Thr
            545                 550                 555 aat tgg cta tgg tat ata aaa ata ttc ata ata gta gga ggc ttg        1849
Asn Trp Leu Trp Tyr Ile Lys Ile Phe Ile Ile Val Gly Gly Leu
        560                 565                 570 ata ggc ttg aga ata att ttt gct gtg ctt tgt ata gta aat aga gtt    1897
Ile Gly Leu Arg Ile Ile Phe Ala Val Leu Cys Ile Val Asn Arg Val
575                 580                 585 aag gca gga tac tca cct ttg tcg ttt cag acc cttacccga accc         1944
Lys Ala Gly Tyr Ser Pro Leu Ser Phe Gln Thr
590                 595                 600

<210> SEQ ID NO: 4
<211> LENGTH: 600
<212> TYPE: PRT
<213> ORGANISM: Human immunodeficiency virus
<220> FEATURE:
<223> OTHER INFORMATION: HIV-1(D747)
```

-continued

<400> SEQUENCE: 4

```
Ser Leu Trp Asp Gln Ser Leu Lys Pro Cys Val Lys Leu Thr Pro Leu
 1               5                  10                  15

Cys Val Thr Leu His Cys Thr Asn Ala Thr Tyr Ser Asn Ser Thr Tyr
                20                  25                  30

Asn Ser Thr Tyr Asn Glu Glu Ile Lys Asn Cys Ser Phe Asn Thr Thr
            35                  40                  45

Thr Glu Leu Arg Asp Lys Lys Gln Lys Val Gln Ala Leu Phe Tyr Lys
         50                  55                  60

Leu Asp Val Val Pro Leu Asn Thr Thr Asp Asn Ser Ser Tyr Arg Leu
 65                  70                  75                  80

Ile Asn Cys Asn Thr Ser Ala Ile Thr Gln Ala Cys Pro Lys Val Ser
                85                  90                  95

Phe Asp Pro Ile Pro Ile His Tyr Cys Ala Gly Ala Gly Tyr Ala Ile
            100                 105                 110

Leu Lys Cys Asn Asn Lys Thr Phe Asn Gly Thr Gly Pro Cys His Asn
        115                 120                 125

Ile Ser Thr Val Gln Cys Thr His Gly Ile Lys Pro Val Val Ser Thr
130                 135                 140

Gln Leu Leu Asn Gly Ser Leu Ala Glu Gly Glu Ile Ile Ile Arg
145                 150                 155                 160

Ser Glu Asn Leu Thr Asn Asn Val Lys Thr Ile Ile Val His Leu Asn
                165                 170                 175

Gln Ser Val Glu Ile Val Tyr Thr Arg Pro Asn Asn Asn Thr Arg Lys
            180                 185                 190

Gly Val Arg Ile Gly Pro Gly Gln Thr Phe Tyr Ala Thr Gly Asp Ile
        195                 200                 205

Ile Gly Asp Ile Arg Gln Ala His Cys Asn Ile Ser Lys His Lys Trp
210                 215                 220

Asn Glu Thr Leu Gln Arg Val Gly Lys Lys Leu Ala Glu His Phe Pro
225                 230                 235                 240

Asn Lys Thr Ile Arg Phe Ala Ser Ser Ser Gly Gly Asp Leu Glu Ile
                245                 250                 255

Thr Thr His Ser Phe Asn Cys Arg Gly Glu Phe Phe Tyr Cys Asn Thr
            260                 265                 270

Ser Asp Leu Phe Asn Gly Thr Tyr Met Pro Asn Gly Thr Lys Ser Asn
        275                 280                 285

Ser Ser Ser Thr Ile Thr Ile Pro Cys Arg Ile Lys Gln Ile Ile Asn
290                 295                 300

Met Trp Gln Glu Val Gly Arg Ala Met Tyr Ala Pro Pro Ile Ala Gly
305                 310                 315                 320

Asn Ile Thr Cys Lys Ser Asn Ile Thr Gly Ile Leu Leu Val Arg Asp
                325                 330                 335

Gly Gly Ile Glu Leu Asn Asp Thr Lys Thr Glu Thr Phe Arg Pro Gly
            340                 345                 350

Gly Gly Glu Met Arg Asp Asn Trp Arg Ser Glu Leu Tyr Lys Tyr Lys
        355                 360                 365

Val Val Glu Ile Lys Pro Leu Gly Val Ala Pro Thr Thr Ala Lys Arg
    370                 375                 380

Arg Val Val Glu Arg Glu Lys Arg Ala Val Gly Ile Gly Ala Val Phe
385                 390                 395                 400

Leu Gly Phe Leu Gly Ala Ala Gly Ser Thr Met Gly Ala Ala Ser Met
            405                 410                 415
```

```
Thr Val Thr Val Gln Ala Arg Gln Leu Leu Ser Gly Ile Val Gln Gln
            420                 425                 430

Gln Ser Asn Leu Leu Arg Ala Ile Glu Ala Gln Gln His Leu Leu Gln
            435                 440                 445

Leu Thr Ile Trp Gly Ile Lys Gln Leu Gln Ala Arg Val Leu Ala Ile
            450                 455                 460

Glu Arg Tyr Leu Lys Glu Gln Gln Leu Leu Gly Ile Trp Gly Cys Ser
465                 470                 475                 480

Gly Lys Leu Ile Cys Thr Thr Val Pro Trp Asn Ser Ser Trp Ser
                485                 490                 495

Asn Arg Ser Gln Thr Asp Ile Trp Asp Asn Met Thr Trp Met Gln Trp
            500                 505                 510

Asp Arg Glu Ile Ser Asn Tyr Thr Glu Thr Ile Tyr Arg Leu Leu Glu
            515                 520                 525

Asp Ser Gln Asn Gln Gln Glu Arg Asn Glu Lys Asp Leu Leu Ala Leu
            530                 535                 540

Asp Ser Trp Lys Asn Leu Trp Asn Trp Phe Ser Ile Thr Asn Trp Leu
545                 550                 555                 560

Trp Tyr Ile Lys Ile Phe Ile Ile Val Gly Gly Leu Ile Gly Leu
                565                 570                 575

Arg Ile Ile Phe Ala Val Leu Cys Ile Val Asn Arg Val Lys Ala Gly
            580                 585                 590

Tyr Ser Pro Leu Ser Phe Gln Thr
            595                 600

<210> SEQ ID NO: 5
<211> LENGTH: 1952
<212> TYPE: DNA
<213> ORGANISM: Human immunodeficiency virus
<220> FEATURE:
<223> OTHER INFORMATION: HIV-1(D760)
<220> FEATURE:
<221> NAME/KEY: CDS
<222> LOCATION: (133)..(1950)

<400> SEQUENCE: 5
cataatgtct gggctacata tgcctgtgta cccacaggcc ccgacccaca agaaatagtt      60
ttggaaaatg taacaggaaa ttttaacatg tggaaaaatg acatggtgga tcaaatgcat     120
gaggatgtaa tc agt tta tgg gat caa agc cta aag cca tgt gta aag ttg     171
            Ser Leu Trp Asp Gln Ser Leu Lys Pro Cys Val Lys Leu
              1               5                  10 acc cca ctc tgt gtc act tta gag tgt gga aat gtt aat gct acc aat     219
Thr Pro Leu Cys Val Thr Leu Glu Cys Gly Asn Val Asn Ala Thr Asn
     15                  20                  25 att acc aat aat ggg gaa aat aat cct acc aat att acc aat aat agg     267
Ile Thr Asn Asn Gly Glu Asn Asn Pro Thr Asn Ile Thr Asn Asn Arg
 30                  35                  40                  45 gaa gaa ata aaa aat tgc cct ttc aat gca acc aca gaa ata aga gat     315
Glu Glu Ile Lys Asn Cys Pro Phe Asn Ala Thr Thr Glu Ile Arg Asp
                 50                  55                  60 agg cag cag aaa gtg tat gca ctt ttt tat aga ctt gat ata gta cca     363
Arg Gln Gln Lys Val Tyr Ala Leu Phe Tyr Arg Leu Asp Ile Val Pro
             65                  70                  75 ctt gat aat aat aat aat agc acc tat aga tta ata aat tgt aat acc     411
Leu Asp Asn Asn Asn Asn Ser Thr Tyr Arg Leu Ile Asn Cys Asn Thr
         80                  85                  90 tca gcc ata aca caa gcc tgt cca aag gtc act ttt gat cca att cct     459
```

```
                                        -continued

Ser Ala Ile Thr Gln Ala Cys Pro Lys Val Thr Phe Asp Pro Ile Pro
 95             100                 105 ata cac tat tgt gct cca gct ggt tat gcg att cta aag tgt aat aat      507
Ile His Tyr Cys Ala Pro Ala Gly Tyr Ala Ile Leu Lys Cys Asn Asn
110             115                 120                 125 aag aca ttc aat ggg aca gga cca tgc cat aat gtc agc aca gta caa      555
Lys Thr Phe Asn Gly Thr Gly Pro Cys His Asn Val Ser Thr Val Gln
                130                 135                 140 tgt aca cat gga att agc cca gtg gta tca act caa cta ctg tta aat      603
Cys Thr His Gly Ile Ser Pro Val Val Ser Thr Gln Leu Leu Leu Asn
            145                 150                 155 ggt agc cta gca gaa gga gag ata ata att aga tct gaa aat ctg aca      651
Gly Ser Leu Ala Glu Gly Glu Ile Ile Ile Arg Ser Glu Asn Leu Thr
        160                 165                 170 gac aat gtc aaa aca ata ata gta cat ctt aat caa tct gta gaa gtt      699
Asp Asn Val Lys Thr Ile Ile Val His Leu Asn Gln Ser Val Glu Val
    175                 180                 185 gtg tgt aca aga ccc aac aat aat aca aga aaa agt ata agg ata gga      747
Val Cys Thr Arg Pro Asn Asn Asn Thr Arg Lys Ser Ile Arg Ile Gly
190             195                 200                 205 cca gga caa aca ttt tat gca aca gga gac ata ata gga gac ata aga      795
Pro Gly Gln Thr Phe Tyr Ala Thr Gly Asp Ile Ile Gly Asp Ile Arg
                210                 215                 220 caa gca cat tgt aac att agt gaa gat aaa tgg aat gaa act tta caa      843
Gln Ala His Cys Asn Ile Ser Glu Asp Lys Trp Asn Glu Thr Leu Gln
            225                 230                 235 agg gta ggt aaa aaa cta gca gaa cac ttc cct aat aaa aca ata aaa      891
Arg Val Gly Lys Lys Leu Ala Glu His Phe Pro Asn Lys Thr Ile Lys
        240                 245                 250 ttt gca gca tcc tca gga ggg gac cta gaa att aca aca tat agt ttt      939
Phe Ala Ala Ser Ser Gly Gly Asp Leu Glu Ile Thr Thr Tyr Ser Phe
    255                 260                 265 aat tgt aga gga gaa ttt ttc tat tgc aat aca tca ggc ctg ttc aat      987
Asn Cys Arg Gly Glu Phe Phe Tyr Cys Asn Thr Ser Gly Leu Phe Asn
270             275                 280                 285 ggt aca tac atg cct aat ggt aca aaa agt aat tta aac tca acc atc     1035
Gly Thr Tyr Met Pro Asn Gly Thr Lys Ser Asn Leu Asn Ser Thr Ile
                290                 295                 300 aca atc cca tgc aga ata aaa caa att gtg aac ctg tgg cag gag gta     1083
Thr Ile Pro Cys Arg Ile Lys Gln Ile Val Asn Leu Trp Gln Glu Val
            305                 310                 315 gga cga gca atg tat gcc cct cca ttt gcc agg aac ata aca tgt aaa     1131
Gly Arg Ala Met Tyr Ala Pro Pro Phe Ala Arg Asn Ile Thr Cys Lys
        320                 325                 330 tca aat atc aca gga cta cta ttg gta cgt gat gga gga gaa gac aca     1179
Ser Asn Ile Thr Gly Leu Leu Leu Val Arg Asp Gly Gly Glu Asp Thr
    335                 340                 345 aat gat aca gag ata ttc agt cct gga gga gga gat atg agg gac aat     1227
Asn Asp Thr Glu Ile Phe Ser Pro Gly Gly Gly Asp Met Arg Asp Asn
350             355                 360                 365 tgg aga agt gaa tta tac aaa tat aaa gtg gta gaa att aag cca ttg     1275
Trp Arg Ser Glu Leu Tyr Lys Tyr Lys Val Val Glu Ile Lys Pro Leu
                370                 375                 380 gga gta gca ccc act aca gca aaa agg aga gtg gtg gag aga gaa aaa     1323
Gly Val Ala Pro Thr Thr Ala Lys Arg Arg Val Val Glu Arg Glu Lys
            385                 390                 395 aga gca gtg gga tta gga gct gtg ttc ctt ggg ttc ttg gga gca gca     1371
Arg Ala Val Gly Leu Gly Ala Val Phe Leu Gly Phe Leu Gly Ala Ala
        400                 405                 410
```

-continued

| | | |
|---|---|---|
| gga agc act atg ggc gcg gcg tca ata acg ctg acg gta cag gcc aga<br>Gly Ser Thr Met Gly Ala Ala Ser Ile Thr Leu Thr Val Gln Ala Arg<br>     415                     420                    425 | | 1419 |
| caa tta ctg tct ggt ata gtg caa cag caa agc aat ttg ctg agg gct<br>Gln Leu Leu Ser Gly Ile Val Gln Gln Gln Ser Asn Leu Leu Arg Ala<br>430                     435                     440                    445 | | 1467 |
| ata gag gcg caa cag cat ctg ttg caa ctc acg gtc tgg ggc att aag<br>Ile Glu Ala Gln Gln His Leu Leu Gln Leu Thr Val Trp Gly Ile Lys<br>                   450                     455                    460 | | 1515 |
| cag ctc cag aca aga gtc ctg gct ata gaa aga tac cta aag gat caa<br>Gln Leu Gln Thr Arg Val Leu Ala Ile Glu Arg Tyr Leu Lys Asp Gln<br>          465                     470                    475 | | 1563 |
| cag ctc cta ggg atg tgg ggc tgc tct gga aaa ctc atc tgc acc act<br>Gln Leu Leu Gly Met Trp Gly Cys Ser Gly Lys Leu Ile Cys Thr Thr<br>     480                     485                     490 | | 1611 |
| gct gta cct tgg aac tcc agt tgg agt aac aga tct caa aca gat att<br>Ala Val Pro Trp Asn Ser Ser Trp Ser Asn Arg Ser Gln Thr Asp Ile<br>              495                     500                    505 | | 1659 |
| tgg gat aac atg acc tgg atg cag tgg gat agg gaa att agt aat tac<br>Trp Asp Asn Met Thr Trp Met Gln Trp Asp Arg Glu Ile Ser Asn Tyr<br>510                     515                     520                    525 | | 1707 |
| aca aat aca ata tac agg ttg ctt gaa gac tcg caa aac cag cag gaa<br>Thr Asn Thr Ile Tyr Arg Leu Leu Glu Asp Ser Gln Asn Gln Gln Glu<br>                   530                     535                    540 | | 1755 |
| aga aat gaa aaa gat tta tta gca ttg gac agt tgg aaa aat ctg tgg<br>Arg Asn Glu Lys Asp Leu Leu Ala Leu Asp Ser Trp Lys Asn Leu Trp<br>          545                     550                    555 | | 1803 |
| aat tgg ttt agc ata aca aat tgg ctg tgg tat ata aaa ata ttc ata<br>Asn Trp Phe Ser Ile Thr Asn Trp Leu Trp Tyr Ile Lys Ile Phe Ile<br>              560                     565                    570 | | 1851 |
| atg ata gta gga ggc ttg ata ggt ttg aga ata att ttt gct gtg ctc<br>Met Ile Val Gly Gly Leu Ile Gly Leu Arg Ile Ile Phe Ala Val Leu<br>575                     580                     585 | | 1899 |
| tct ata gtg aat aga gtt agg cag gga tac tca cct ttg tcg ttt cag<br>Ser Ile Val Asn Arg Val Arg Gln Gly Tyr Ser Pro Leu Ser Phe Gln<br>590                     595                     600                    605 | | 1947 |
| acc ct<br>Thr | | 1952 |

<210> SEQ ID NO: 6
<211> LENGTH: 606
<212> TYPE: PRT
<213> ORGANISM: Human immunodeficiency virus
<220> FEATURE:
<223> OTHER INFORMATION: HIV-1(D760)

<400> SEQUENCE: 6

Ser Leu Trp Asp Gln Ser Leu Lys Pro Cys Val Lys Leu Thr Pro Leu
 1               5                  10                  15

Cys Val Thr Leu Glu Cys Gly Asn Val Asn Ala Thr Asn Ile Thr Asn
                20                  25                  30

Asn Gly Glu Asn Pro Thr Asn Ile Thr Asn Asn Arg Glu Glu Ile
            35                  40                  45

Lys Asn Cys Pro Phe Asn Ala Thr Thr Glu Ile Arg Asp Arg Gln Gln
        50                  55                  60

Lys Val Tyr Ala Leu Phe Tyr Arg Leu Asp Ile Val Pro Leu Asp Asn
    65                  70                  75                  80

Asn Asn Asn Ser Thr Tyr Arg Leu Ile Asn Cys Asn Thr Ser Ala Ile
                85                  90                  95

-continued

```
Thr Gln Ala Cys Pro Lys Val Thr Phe Asp Pro Ile Pro Ile His Tyr
            100                 105                 110
Cys Ala Pro Ala Gly Tyr Ala Ile Leu Lys Cys Asn Asn Lys Thr Phe
            115                 120                 125
Asn Gly Thr Gly Pro Cys His Asn Val Ser Thr Val Gln Cys Thr His
            130                 135                 140
Gly Ile Ser Pro Val Val Ser Thr Gln Leu Leu Leu Asn Gly Ser Leu
145                 150                 155                 160
Ala Glu Gly Glu Ile Ile Ile Arg Ser Glu Asn Leu Thr Asp Asn Val
                    165                 170                 175
Lys Thr Ile Ile Val His Leu Asn Gln Ser Val Glu Val Val Cys Thr
                    180                 185                 190
Arg Pro Asn Asn Asn Thr Arg Lys Ser Ile Arg Ile Gly Pro Gly Gln
            195                 200                 205
Thr Phe Tyr Ala Thr Gly Asp Ile Ile Gly Asp Ile Arg Gln Ala His
            210                 215                 220
Cys Asn Ile Ser Glu Asp Lys Trp Asn Glu Thr Leu Gln Arg Val Gly
225                 230                 235                 240
Lys Lys Leu Ala Glu His Phe Pro Asn Lys Thr Ile Lys Phe Ala Ala
                    245                 250                 255
Ser Ser Gly Gly Asp Leu Glu Ile Thr Thr Tyr Ser Phe Asn Cys Arg
            260                 265                 270
Gly Glu Phe Phe Tyr Cys Asn Thr Ser Gly Leu Phe Asn Gly Thr Tyr
            275                 280                 285
Met Pro Asn Gly Thr Lys Ser Asn Leu Asn Ser Thr Ile Thr Ile Pro
            290                 295                 300
Cys Arg Ile Lys Gln Ile Val Asn Leu Trp Gln Glu Val Gly Arg Ala
305                 310                 315                 320
Met Tyr Ala Pro Pro Phe Ala Arg Asn Ile Thr Cys Lys Ser Asn Ile
                    325                 330                 335
Thr Gly Leu Leu Leu Val Arg Asp Gly Gly Glu Asp Thr Asn Asp Thr
            340                 345                 350
Glu Ile Phe Ser Pro Gly Gly Gly Asp Met Arg Asp Asn Trp Arg Ser
            355                 360                 365
Glu Leu Tyr Lys Tyr Lys Val Val Glu Ile Lys Pro Leu Gly Val Ala
            370                 375                 380
Pro Thr Thr Ala Lys Arg Arg Val Val Glu Arg Glu Lys Arg Ala Val
385                 390                 395                 400
Gly Leu Gly Ala Val Phe Leu Gly Phe Leu Gly Ala Ala Gly Ser Thr
                    405                 410                 415
Met Gly Ala Ala Ser Ile Thr Leu Thr Val Gln Ala Arg Gln Leu Leu
                    420                 425                 430
Ser Gly Ile Val Gln Gln Ser Asn Leu Leu Arg Ala Ile Glu Ala
            435                 440                 445
Gln Gln His Leu Leu Gln Leu Thr Val Trp Gly Ile Lys Gln Leu Gln
            450                 455                 460
Thr Arg Val Leu Ala Ile Glu Arg Tyr Leu Lys Asp Gln Gln Leu Leu
465                 470                 475                 480
Gly Met Trp Gly Cys Ser Gly Lys Leu Ile Cys Thr Thr Ala Val Pro
                    485                 490                 495
Trp Asn Ser Ser Trp Ser Asn Arg Ser Gln Thr Asp Ile Trp Asp Asn
            500                 505                 510
Met Thr Trp Met Gln Trp Asp Arg Glu Ile Ser Asn Tyr Thr Asn Thr
```

```
                515                 520                 525
Ile Tyr Arg Leu Leu Glu Asp Ser Gln Asn Gln Gln Glu Arg Asn Glu
            530                 535                 540

Lys Asp Leu Leu Ala Leu Asp Ser Trp Lys Asn Leu Trp Asn Trp Phe
545                 550                 555                 560

Ser Ile Thr Asn Trp Leu Trp Tyr Ile Lys Ile Phe Ile Met Ile Val
                565                 570                 575

Gly Gly Leu Ile Gly Leu Arg Ile Ile Phe Ala Val Leu Ser Ile Val
            580                 585                 590

Asn Arg Val Arg Gln Gly Tyr Ser Pro Leu Ser Phe Gln Thr
            595                 600                 605

<210> SEQ ID NO: 7
<211> LENGTH: 9
<212> TYPE: PRT
<213> ORGANISM: Human immunodeficiency virus

<400> SEQUENCE: 7

Met Pro Asn Gly Thr Lys Ser Asn Ser
 1               5

<210> SEQ ID NO: 8
<211> LENGTH: 9
<212> TYPE: PRT
<213> ORGANISM: Human immunodeficiency virus

<400> SEQUENCE: 8

Met Pro Asn Gly Thr Lys Gly Asn Ser
 1               5

<210> SEQ ID NO: 9
<211> LENGTH: 9
<212> TYPE: PRT
<213> ORGANISM: Human immunodeficiency virus

<400> SEQUENCE: 9

Met Pro Asn Gly Thr Lys Ser Asn Leu
 1               5

<210> SEQ ID NO: 10
<211> LENGTH: 14
<212> TYPE: PRT
<213> ORGANISM: Human immunodeficiency virus

<400> SEQUENCE: 10

Arg Asn Glu Lys Asp Leu Leu Ala Leu Asp Ser Trp Lys Asn
 1               5                  10

<210> SEQ ID NO: 11
<211> LENGTH: 615
<212> TYPE: PRT
<213> ORGANISM: Human immunodeficiency virus
<220> FEATURE:
<223> OTHER INFORMATION: HIV-1(Bru)

<400> SEQUENCE: 11

Ser Leu Trp Asp Gln Ser Leu Lys Pro Cys Val Lys Leu Thr Pro Leu
 1               5                  10                  15

Cys Val Ser Leu Lys Cys Thr Asp Leu Gly Asn Ala Thr Asn Thr Asn
            20                  25                  30

Ser Ser Asn Thr Asn Ser Ser Ser Gly Glu Met Met Met Glu Lys Gly
        35                  40                  45
```

-continued

```
Glu Ile Lys Asn Cys Ser Phe Asn Ile Ser Thr Ser Ile Arg Gly Lys
 50                  55                  60
Val Gln Lys Glu Tyr Ala Phe Phe Tyr Lys Leu Asp Ile Ile Pro Ile
 65                  70                  75                  80
Asp Asn Asp Thr Thr Ser Tyr Thr Leu Thr Ser Cys Asn Thr Ser Val
                 85                  90                  95
Ile Thr Gln Ala Cys Pro Lys Val Ser Phe Glu Pro Ile Pro Ile His
                100                 105                 110
Tyr Cys Ala Pro Ala Gly Phe Ala Ile Leu Lys Cys Asn Asn Lys Thr
                115                 120                 125
Phe Asn Gly Thr Gly Pro Cys Thr Asn Val Ser Thr Val Gln Cys Thr
130                 135                 140
His Gly Ile Arg Pro Val Val Ser Thr Gln Leu Leu Leu Asn Gly Ser
145                 150                 155                 160
Leu Ala Glu Glu Glu Val Val Ile Arg Ser Ala Asn Phe Thr Asp Asn
                165                 170                 175
Ala Lys Thr Ile Ile Val Gln Leu Asn Gln Ser Val Glu Ile Asn Cys
                180                 185                 190
Thr Arg Pro Asn Asn Asn Thr Arg Lys Ser Ile Arg Ile Gln Arg Gly
                195                 200                 205
Pro Gly Arg Ala Phe Val Thr Ile Gly Lys Ile Gly Asn Met Arg Gln
210                 215                 220
Ala His Cys Asn Ile Ser Arg Ala Lys Trp Asn Ala Thr Leu Lys Gln
225                 230                 235                 240
Ile Ala Ser Lys Leu Arg Glu Gln Phe Gly Asn Asn Lys Thr Ile Ile
                245                 250                 255
Phe Lys Gln Ser Ser Gly Gly Asp Pro Glu Ile Val Thr His Ser Phe
                260                 265                 270
Asn Cys Gly Gly Glu Phe Phe Tyr Cys Asn Ser Thr Gln Leu Phe Asn
                275                 280                 285
Ser Thr Trp Phe Asn Ser Thr Trp Ser Thr Glu Gly Ser Asn Asn Thr
                290                 295                 300
Glu Gly Ser Asp Thr Ile Thr Leu Pro Cys Arg Ile Lys Gln Phe Ile
305                 310                 315                 320
Asn Met Trp Gln Glu Val Gly Lys Ala Met Tyr Ala Pro Pro Ile Ser
                325                 330                 335
Gly Gln Ile Arg Cys Ser Ser Asn Ile Thr Gly Leu Leu Leu Thr Arg
                340                 345                 350
Asp Gly Gly Asn Asn Asn Gly Ser Glu Ile Phe Arg Pro Gly Gly Gly
                355                 360                 365
Gly Asp Met Arg Asp Asn Trp Arg Ser Glu Leu Tyr Lys Tyr Lys Val
                370                 375                 380
Val Lys Ile Glu Pro Leu Gly Val Ala Pro Thr Lys Ala Lys Arg Arg
385                 390                 395                 400
Val Val Gln Arg Glu Lys Arg Ala Val Gly Ile Gly Ala Leu Phe Leu
                405                 410                 415
Gly Phe Leu Gly Ala Ala Gly Ser Thr Met Gly Ala Arg Ser Met Thr
                420                 425                 430
Leu Thr Val Gln Ala Arg Gln Leu Leu Ser Gly Ile Val Gln Gln Gln
                435                 440                 445
Asn Asn Leu Leu Arg Ala Ile Glu Ala Gln Gln His Leu Leu Gln Leu
                450                 455                 460
```

-continued

```
Thr Val Trp Gly Ile Lys Gln Leu Gln Ala Arg Ile Leu Ala Val Glu
465                 470                 475                 480

Arg Tyr Leu Lys Asp Gln Gln Leu Leu Gly Ile Trp Gly Cys Ser Gly
                485                 490                 495

Lys Leu Ile Cys Thr Thr Ala Val Pro Trp Asn Ala Ser Trp Ser Asn
                500                 505                 510

Lys Ser Leu Glu Gln Ile Trp Asn Asn Met Thr Trp Met Glu Trp Asp
                515                 520                 525

Arg Glu Ile Asn Asn Tyr Thr Ser Leu Ile His Ser Leu Ile Glu Glu
            530                 535                 540

Ser Gln Asn Gln Gln Glu Lys Asn Glu Gln Glu Leu Leu Glu Leu Asp
545                 550                 555                 560

Lys Trp Ala Ser Leu Trp Asn Trp Phe Asn Ile Thr Asn Trp Leu Trp
                565                 570                 575

Tyr Ile Lys Ile Phe Ile Met Ile Val Gly Gly Leu Val Gly Leu Arg
                580                 585                 590

Ile Val Phe Ala Val Leu Ser Ile Val Asn Arg Val Arg Gln Gly Tyr
                595                 600                 605

Ser Pro Leu Ser Phe Gln Thr
610                 615

<210> SEQ ID NO: 12
<211> LENGTH: 610
<212> TYPE: PRT
<213> ORGANISM: Human immunodeficiency virus
<220> FEATURE:
<223> OTHER INFORMATION: HIV-1(SF2)

<400> SEQUENCE: 12

Ser Leu Trp Asp Gln Ser Leu Lys Pro Cys Val Lys Leu Thr Pro Leu
1               5                   10                  15

Cys Val Thr Leu Asn Cys Thr Asp Leu Gly Lys Ala Thr Asn Thr Asn
                20                  25                  30

Ser Ser Asn Trp Lys Glu Glu Ile Lys Gly Glu Ile Lys Asn Cys Ser
                35                  40                  45

Phe Asn Ile Thr Thr Ser Ile Arg Asp Lys Ile Gln Lys Glu Asn Ala
            50                  55                  60

Leu Phe Arg Asn Leu Asp Val Val Pro Ile Asp Asn Ala Ser Thr Thr
65                  70                  75                  80

Thr Asn Tyr Thr Asn Tyr Arg Leu Ile His Cys Asn Arg Ser Val Ile
                85                  90                  95

Thr Gln Ala Cys Pro Lys Val Ser Phe Glu Pro Ile Pro Ile His Tyr
                100                 105                 110

Cys Thr Pro Ala Gly Phe Ala Ile Leu Lys Cys Asn Asn Lys Thr Phe
                115                 120                 125

Asn Gly Lys Gly Pro Cys Thr Asn Val Ser Thr Val Gln Cys Thr His
130                 135                 140

Gly Ile Arg Pro Ile Val Ser Thr Gln Leu Leu Leu Asn Gly Ser Leu
145                 150                 155                 160

Ala Glu Glu Glu Val Val Ile Arg Ser Asp Asn Phe Thr Asn Asn Ala
                165                 170                 175

Lys Thr Ile Ile Val Gln Leu Asn Glu Ser Val Ala Ile Asn Cys Thr
                180                 185                 190

Arg Pro Asn Asn Asn Thr Arg Lys Ser Ile Tyr Ile Gly Pro Gly Arg
                195                 200                 205
```

```
Ala Phe His Thr Thr Gly Arg Ile Ile Gly Asp Ile Arg Lys Ala His
    210                 215                 220

Cys Asn Ile Ser Arg Ala Gln Trp Asn Asn Thr Leu Glu Gln Ile Val
225                 230                 235                 240

Lys Lys Leu Arg Glu Gln Phe Gly Asn Asn Lys Thr Ile Val Phe Asn
                245                 250                 255

Gln Ser Ser Gly Gly Asp Pro Glu Ile Val Met His Ser Phe Asn Cys
            260                 265                 270

Arg Gly Glu Phe Phe Tyr Cys Asn Thr Thr Gln Leu Phe Asn Asn Thr
        275                 280                 285

Trp Arg Leu Asn His Thr Glu Gly Thr Lys Gly Asn Asp Thr Ile Ile
    290                 295                 300

Leu Pro Cys Arg Ile Lys Gln Ile Ile Asn Met Trp Gln Glu Val Gly
305                 310                 315                 320

Lys Ala Met Tyr Ala Pro Pro Ile Gly Gly Gln Ile Ser Cys Ser Ser
                325                 330                 335

Asn Ile Thr Gly Leu Leu Leu Thr Arg Asp Gly Gly Thr Asn Val Thr
            340                 345                 350

Asn Asp Thr Glu Val Phe Arg Pro Gly Gly Gly Asp Met Arg Asp Asn
        355                 360                 365

Trp Arg Ser Glu Leu Tyr Lys Tyr Lys Val Ile Lys Ile Glu Pro Leu
    370                 375                 380

Gly Ile Ala Pro Thr Lys Ala Lys Arg Val Val Gln Arg Glu Lys
385                 390                 395                 400

Arg Ala Val Gly Ile Val Gly Ala Met Phe Leu Gly Phe Leu Gly Ala
                405                 410                 415

Ala Gly Ser Thr Met Gly Ala Val Ser Leu Thr Leu Thr Val Gln Ala
            420                 425                 430

Arg Gln Leu Leu Ser Gly Ile Val Gln Gln Asn Asn Leu Leu Arg
        435                 440                 445

Ala Ile Glu Ala Gln Gln His Leu Leu Gln Leu Thr Val Trp Gly Ile
    450                 455                 460

Lys Gln Leu Gln Ala Arg Val Leu Ala Val Glu Arg Tyr Leu Arg Asp
465                 470                 475                 480

Gln Gln Leu Leu Gly Ile Trp Gly Cys Ser Gly Lys Leu Ile Cys Thr
                485                 490                 495

Thr Ala Val Pro Trp Asn Ala Ser Trp Ser Asn Lys Ser Leu Glu Asp
            500                 505                 510

Ile Trp Asp Asn Met Thr Trp Met Gln Trp Glu Arg Glu Ile Asp Asn
        515                 520                 525

Tyr Thr Asn Thr Ile Tyr Thr Leu Leu Glu Glu Ser Gln Asn Gln Gln
    530                 535                 540

Glu Lys Asn Glu Gln Glu Leu Leu Glu Leu Asp Lys Trp Ala Ser Leu
545                 550                 555                 560

Trp Asn Trp Phe Ser Ile Thr Asn Trp Leu Trp Tyr Ile Lys Ile Phe
                565                 570                 575

Ile Met Ile Val Gly Gly Leu Val Gly Leu Arg Ile Val Phe Ala Val
            580                 585                 590

Leu Ser Ile Val Asn Arg Val Arg Gln Gly Tyr Ser Pro Leu Ser Phe
        595                 600                 605

Gln Thr
    610
```

-continued

```
<210> SEQ ID NO: 13
<211> LENGTH: 608
<212> TYPE: PRT
<213> ORGANISM: Human immunodeficiency virus
<220> FEATURE:
<223> OTHER INFORMATION: HIV-1(Eli)

<400> SEQUENCE: 13

Ser Leu Trp Asp Gln Ser Leu Lys Pro Cys Val Lys Leu Thr Pro Leu
  1               5                  10                  15

Cys Val Thr Leu Asn Cys Ser Asp Glu Leu Arg Asn Asn Gly Thr Met
             20                  25                  30

Gly Asn Asn Val Thr Thr Glu Glu Lys Gly Met Lys Asn Cys Ser Phe
         35                  40                  45

Asn Val Thr Thr Val Leu Lys Asp Lys Lys Gln Gln Val Tyr Ala Leu
 50                  55                  60

Phe Tyr Arg Leu Asp Ile Val Pro Ile Asp Asn Asp Ser Ser Thr Asn
 65                  70                  75                  80

Ser Thr Asn Tyr Arg Leu Ile Asn Cys Asn Thr Ser Ala Ile Thr Gln
                 85                  90                  95

Ala Cys Pro Lys Val Ser Phe Glu Pro Ile Pro Ile His Tyr Cys Ala
            100                 105                 110

Pro Ala Gly Phe Ala Ile Leu Lys Cys Arg Asp Lys Lys Phe Asn Gly
        115                 120                 125

Thr Gly Pro Cys Thr Asn Val Ser Thr Val Gln Cys Thr His Gly Ile
    130                 135                 140

Arg Pro Val Val Ser Thr Gln Leu Leu Leu Asn Gly Ser Leu Ala Glu
145                 150                 155                 160

Glu Glu Val Ile Ile Arg Ser Glu Asn Leu Thr Asn Asn Ala Lys Asn
                165                 170                 175

Ile Ile Ala His Leu Asn Glu Ser Val Lys Ile Thr Cys Ala Arg Pro
            180                 185                 190

Tyr Gln Asn Thr Arg Gln Arg Thr Pro Ile Gly Leu Gly Gln Ser Leu
        195                 200                 205

Tyr Thr Thr Arg Ser Arg Ser Ile Ile Gly Gln Ala His Cys Asn Ile
    210                 215                 220

Ser Arg Ala Gln Trp Ser Lys Thr Leu Gln Gln Val Ala Arg Lys Leu
225                 230                 235                 240

Gly Thr Leu Leu Asn Lys Thr Ile Ile Lys Phe Lys Pro Ser Ser Gly
                245                 250                 255

Gly Asp Pro Glu Ile Thr Thr His Ser Phe Asn Cys Gly Gly Glu Phe
            260                 265                 270

Phe Tyr Cys Asn Thr Ser Gly Leu Phe Asn Ser Thr Trp Asn Ile Ser
        275                 280                 285

Ala Trp Asn Asn Ile Thr Glu Ser Asn Asn Ser Thr Asn Thr Asn Ile
    290                 295                 300

Thr Leu Gln Cys Arg Ile Lys Gln Ile Ile Lys Met Val Ala Gly Arg
305                 310                 315                 320

Lys Ala Ile Tyr Ala Pro Pro Ile Glu Arg Asn Ile Leu Cys Ser Ser
                325                 330                 335

Asn Ile Thr Gly Leu Leu Leu Thr Arg Asp Gly Ile Asn Asn Ser
            340                 345                 350

Thr Asn Glu Thr Phe Arg Pro Gly Gly Gly Asp Met Arg Asp Asn Trp
        355                 360                 365

Arg Ser Glu Leu Tyr Lys Tyr Lys Val Val Gln Ile Glu Pro Leu Gly
```

-continued

```
                    370                 375                 380
Val Ala Pro Thr Arg Ala Lys Arg Val Val Glu Arg Glu Lys Arg
385                 390                 395                 400

Ala Ile Gly Leu Gly Ala Met Phe Leu Gly Phe Leu Gly Ala Ala Gly
                    405                 410                 415

Ser Thr Met Gly Ala Arg Ser Val Thr Leu Thr Val Gln Ala Arg Gln
                    420                 425                 430

Leu Met Ser Gly Ile Val Gln Gln Asn Asn Leu Leu Arg Ala Ile
                    435                 440                 445

Glu Ala Gln Gln His Leu Leu Gln Leu Thr Val Trp Gly Ile Lys Gln
        450                 455                 460

Leu Gln Ala Arg Ile Leu Ala Val Glu Arg Tyr Leu Lys Asp Gln Gln
465                 470                 475                 480

Leu Leu Gly Ile Trp Gly Cys Ser Gly Lys His Ile Cys Thr Thr Asn
                    485                 490                 495

Val Pro Trp Asn Ser Ser Trp Ser Asn Arg Ser Leu Asn Glu Ile Trp
                    500                 505                 510

Gln Asn Met Thr Trp Met Glu Trp Glu Arg Glu Ile Asp Asn Tyr Thr
                    515                 520                 525

Gly Leu Ile Tyr Ser Leu Ile Glu Glu Ser Gln Thr Gln Gln Glu Lys
                    530                 535                 540

Asn Glu Lys Glu Leu Leu Glu Leu Asp Lys Trp Ala Ser Leu Trp Asn
545                 550                 555                 560

Trp Phe Ser Ile Thr Gln Trp Leu Trp Tyr Ile Lys Ile Phe Ile Met
                    565                 570                 575

Ile Ile Gly Gly Leu Ile Gly Leu Arg Ile Val Phe Ala Val Leu Ser
                    580                 585                 590

Leu Val Asn Arg Val Arg Gln Gly Tyr Ser Pro Leu Ser Phe Gln Thr
                    595                 600                 605
```

<210> SEQ ID NO: 14
<211> LENGTH: 613
<212> TYPE: PRT
<213> ORGANISM: Human immunodeficiency virus
<220> FEATURE:
<223> OTHER INFORMATION: HIV-1(Mal)

<400> SEQUENCE: 14

```
Ser Leu Trp Asp Gln Ser Leu Lys Pro Cys Val Lys Leu Thr Pro Leu
1               5                   10                  15

Cys Val Thr Leu Asn Cys Thr Asn Val Asn Gly Thr Ala Val Asn Gly
                20                  25                  30

Thr Asn Ala Gly Ser Asn Arg Thr Asn Ala Glu Leu Lys Met Glu Ile
                35                  40                  45

Gly Glu Val Lys Asn Cys Ser Phe Asn Ile Thr Pro Val Gly Ser Asp
            50                  55                  60

Lys Arg Gln Glu Tyr Ala Thr Phe Tyr Asn Leu Asp Leu Val Gln Ile
65                  70                  75                  80

Asp Asp Ser Asp Asn Ser Ser Tyr Arg Leu Ile Asn Cys Asn Thr Ser
                    85                  90                  95

Val Ile Thr Gln Ala Cys Pro Lys Val Thr Phe Asp Pro Ile Pro Ile
                100                 105                 110

His Tyr Cys Ala Pro Ala Gly Phe Ala Ile Leu Lys Cys Asn Asp Lys
            115                 120                 125

Lys Phe Asn Gly Thr Glu Ile Cys Lys Asn Val Ser Thr Val Gln Cys
```

-continued

```
            130                 135                 140
Thr His Gly Ile Lys Pro Val Val Ser Thr Gln Leu Leu Leu Asn Gly
145                 150                 155                 160
Ser Leu Ala Glu Glu Ile Met Ile Arg Ser Glu Asn Leu Thr Asp
                165                 170                 175
Asn Thr Lys Asn Ile Ile Val Gln Leu Asn Glu Thr Val Thr Ile Asn
                180                 185                 190
Cys Thr Arg Pro Gly Asn Asn Thr Arg Arg Gly Ile His Phe Gly Pro
                195                 200                 205
Gly Gln Ala Leu Tyr Thr Thr Gly Ile Val Gly Asp Ile Arg Arg Ala
            210                 215                 220
Tyr Cys Thr Ile Asn Glu Thr Glu Trp Asp Lys Thr Leu Gln Gln Val
225                 230                 235                 240
Ala Val Lys Leu Gly Ser Leu Leu Asn Lys Thr Lys Ile Ile Phe Asn
                245                 250                 255
Ser Ser Ser Gly Gly Asp Pro Glu Ile Thr Thr His Ser Phe Asn Cys
                260                 265                 270
Arg Gly Glu Phe Phe Tyr Cys Asn Thr Ser Lys Leu Phe Asn Ser Thr
            275                 280                 285
Trp Gln Asn Asn Gly Ala Arg Leu Ser Asn Ser Thr Glu Ser Thr Gly
            290                 295                 300
Ser Ile Thr Leu Pro Cys Arg Ile Lys Gln Ile Ile Asn Met Trp Gln
305                 310                 315                 320
Lys Thr Gly Lys Ala Met Tyr Ala Pro Pro Ile Ala Gly Val Ile Asn
                325                 330                 335
Cys Leu Ser Asn Ile Thr Gly Leu Ile Leu Thr Arg Asp Gly Gly Asn
                340                 345                 350
Ser Ser Asp Asn Ser Asp Asn Glu Thr Leu Arg Pro Gly Gly Gly Asp
                355                 360                 365
Met Arg Asp Asn Trp Ile Ser Glu Leu Tyr Lys Tyr Lys Val Val Arg
            370                 375                 380
Ile Glu Pro Leu Gly Val Ala Pro Thr Lys Ala Lys Arg Arg Val Val
385                 390                 395                 400
Glu Arg Glu Lys Arg Ala Ile Gly Leu Gly Ala Met Phe Leu Gly Phe
                405                 410                 415
Leu Gly Ala Ala Gly Ser Thr Met Gly Ala Ala Ser Leu Thr Leu Thr
                420                 425                 430
Val Gln Ala Arg Gln Leu Leu Ser Gly Ile Val Gln Gln Gln Asn Asn
                435                 440                 445
Leu Leu Arg Ala Ile Glu Ala Gln Gln His Leu Leu Gln Leu Thr Val
            450                 455                 460
Trp Gly Ile Lys Gln Leu Gln Ala Arg Val Leu Ala Val Glu Arg Tyr
465                 470                 475                 480
Leu Gln Asp Gln Arg Leu Leu Gly Met Trp Gly Cys Ser Gly Lys His
                485                 490                 495
Ile Cys Thr Thr Phe Val Pro Trp Asn Ser Ser Trp Ser Asn Arg Ser
                500                 505                 510
Leu Asp Asp Ile Trp Asn Asn Met Thr Trp Met Gln Trp Glu Lys Glu
                515                 520                 525
Ile Ser Asn Tyr Thr Gly Ile Ile Tyr Asn Leu Ile Glu Glu Ser Gln
                530                 535                 540
Ile Gln Gln Glu Lys Asn Glu Lys Glu Leu Leu Glu Leu Asp Lys Trp
545                 550                 555                 560
```

-continued

```
Ala Ser Leu Trp Asn Trp Phe Ser Ile Ser Lys Trp Leu Trp Tyr Ile
            565                 570                 575

Arg Ile Phe Ile Ile Val Val Gly Gly Leu Ile Gly Leu Arg Ile Ile
            580                 585                 590

Phe Ala Val Leu Ser Leu Val Asn Arg Val Arg Gln Gly Tyr Ser Pro
            595                 600                 605

Leu Ser Leu Gln Thr
        610

<210> SEQ ID NO: 15
<211> LENGTH: 602
<212> TYPE: PRT
<213> ORGANISM: Simian immunodeficiency virus
<220> FEATURE:
<223> OTHER INFORMATION: SIVcpz

<400> SEQUENCE: 15

Ser Leu Trp Asp Gln Ser Leu Lys Pro Cys Val Lys Leu Thr Pro Leu
 1               5                  10                  15

Cys Val Thr Leu Gln Cys Ser Lys Ala Asn Phe Ser Gln Ala Lys Asn
            20                  25                  30

Leu Thr Asn Gln Thr Ser Ser Pro Leu Glu Met Lys Asn Cys Ser
        35                  40                  45

Phe Asn Val Thr Thr Glu Leu Arg Asp Lys Lys Gln Val Tyr Ser
    50                  55                  60

Leu Phe Tyr Val Glu Asp Val Val Asn Leu Gly Asn Glu Asn Asn Thr
 65                  70                  75                  80

Tyr Arg Ile Ile Asn Cys Asn Thr Thr Ala Ile Thr Gln Ala Cys Pro
                85                  90                  95

Lys Thr Ser Phe Glu Pro Ile Pro Ile His Tyr Cys Ala Pro Ala Gly
            100                 105                 110

Phe Ala Ile Leu Lys Cys Asn Asp Lys Asp Phe Ser Gly Lys Gly Lys
        115                 120                 125

Cys Thr Asn Val Ser Thr Val His Cys Thr His Gly Ile Lys Pro Val
    130                 135                 140

Val Thr Thr Gln Leu Leu Ile Asn Gly Ser Leu Ala Glu Gly Asn Ile
145                 150                 155                 160

Thr Val Arg Val Glu Asn Lys Ser Lys Asn Thr Asp Val Trp Ile Val
                165                 170                 175

Gln Leu Val Glu Ala Val Ser Leu Asn Cys His Arg Pro Gly Asn Asn
            180                 185                 190

Thr Arg Gly Glu Val Gln Ile Gly Pro Gly Met Thr Phe Tyr Asn Ile
        195                 200                 205

Glu Asn Val Val Gly Asp Thr Arg Ser Ala Tyr Cys Lys Ile Asn Gly
    210                 215                 220

Thr Thr Trp Asn Arg Thr Val Glu Glu Val Lys Lys Ala Leu Ala Thr
225                 230                 235                 240

Ser Ser Asn Arg Thr Ala Ala Asn Ile Thr Leu Asn Arg Ala Ser Gly
                245                 250                 255

Gly Asp Pro Glu Val Thr His His Met Phe Asn Cys Gly Gly Glu Phe
            260                 265                 270

Phe Tyr Cys Asn Thr Ser Gln Ile Phe Thr Asp Asn Ile Thr Asn Gly
        275                 280                 285

Ile Ile Ile Leu Pro Cys Arg Ile Arg Gln Ile Val Ser Ser Trp Met
    290                 295                 300
```

-continued

```
Arg Val Gly Arg Gly Ile Tyr Ala Pro Pro Ile Arg Gly Asn Ile Thr
305             310             315             320

Cys Asn Ser Asn Ile Thr Gly Leu Leu Leu Thr Ser Asp Thr Pro Val
            325             330             335

Thr Asn Asn Ser Gly Asn Leu Thr Phe Arg Pro Thr Gly Gly Asn Met
            340             345             350

Lys Asp Ile Trp Arg Ser Glu Leu Tyr Lys Tyr Lys Val Val Arg Ile
            355             360             365

Glu Pro Leu Ser Val Ala Pro Thr Lys Ala Arg Arg His Thr Val Ala
    370             375             380

Arg Gln Lys Asp Arg Gln Lys Arg Ala Ala Phe Gly Leu Gly Ala Leu
385             390             395             400

Phe Leu Gly Phe Leu Gly Ala Ala Gly Ser Thr Met Gly Ala Ala Ala
            405             410             415

Val Thr Leu Thr Val Gln Ala Arg Gln Leu Leu Ser Gly Ile Val Gln
            420             425             430

Gln Gln Asn Asn Leu Leu Lys Ala Ile Glu Ala Gln Gln His Leu Leu
            435             440             445

Gln Leu Ser Ile Trp Gly Val Lys Gln Leu Gln Ala Arg Leu Leu Ala
    450             455             460

Val Glu Arg Tyr Leu Gln Asp Gln Gln Ile Leu Gly Leu Trp Gly Cys
465             470             475             480

Ser Gly Lys Ala Val Cys Tyr Thr Thr Val Pro Trp Asn Asn Ser Trp
            485             490             495

Pro Gly Ser Asn Ser Thr Asp Asp Ile Trp Gly Asn Leu Thr Trp Gln
            500             505             510

Gln Trp Asp Lys Leu Val Ser Asn Tyr Thr Gly Lys Ile Phe Gly Leu
    515             520             525

Leu Glu Glu Ala Gln Ser Gln Gln Glu Lys Asn Glu Arg Asp Leu Leu
    530             535             540

Glu Leu Asp Gln Trp Ala Ser Leu Trp Asn Trp Phe Asp Ile Thr Lys
545             550             555             560

Trp Leu Trp Tyr Ile Lys Ile Phe Leu Met Ala Val Gly Gly Ile Ile
            565             570             575

Gly Leu Arg Ile Ile Met Thr Val Phe Ser Val Val Arg Arg Val Arg
            580             585             590

Gln Gly Tyr Ser Pro Leu Ser Leu Gln Thr
            595             600
```